United States Patent
Reddy et al.

(10) Patent No.: US 11,591,597 B2
(45) Date of Patent: Feb. 28, 2023

(54) MICRORNAS AS THERAPEUTIC TARGETS FOR ISCHEMIC STROKE

(71) Applicant: Texas Tech University System, Lubbock, TX (US)

(72) Inventors: P. Hemachandra Reddy, Lubbock, TX (US); Murali Vijayan, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 17/049,041

(22) PCT Filed: Apr. 18, 2019

(86) PCT No.: PCT/US2019/028069
§ 371 (c)(1),
(2) Date: Oct. 20, 2020

(87) PCT Pub. No.: WO2019/204574
PCT Pub. Date: Oct. 24, 2019

(65) Prior Publication Data
US 2021/0238593 A1    Aug. 5, 2021

Related U.S. Application Data

(60) Provisional application No. 62/660,649, filed on Apr. 20, 2018.

(51) Int. Cl.
C12N 15/113   (2010.01)
C12Q 1/6883   (2018.01)
A61P 9/10     (2006.01)

(52) U.S. Cl.
CPC .............. *C12N 15/113* (2013.01); *A61P 9/10* (2018.01); *C12Q 1/6883* (2013.01); *C12N 2310/141* (2013.01); *C12Q 2600/112* (2013.01)

(58) Field of Classification Search
None
See application file for complete search history.

(56) References Cited

U.S. PATENT DOCUMENTS

| | | | |
|---|---|---|---|
| 8,956,817 B2 | 2/2015 | Goel et al. | |
| 2013/0005658 A1* | 1/2013 | Olson | A61P 7/10 514/16.4 |
| 2014/0073684 A1* | 3/2014 | Stoffel | C12N 15/113 514/44 A |
| 2015/0037403 A1* | 2/2015 | Faden | C12N 15/113 435/375 |

FOREIGN PATENT DOCUMENTS

CN    103667445 A    3/2014

OTHER PUBLICATIONS

Feng et al. PLOS ONE 9, e88685, pp. 1-8 (Year: 2014).*
Dias et al. Circulation Journal vol. 80, pp. 1-9 (Year: 2016).*
Allan, L.M. et al. (2011) Long term incidence of dementia, predictors of mortality and pathological diagnosis in older stroke survivors. Brain. 134: 3716-3727.
Alluri, H. et al. (2015) Oxygen-glucose deprivation and reoxygenation as an in vitro ischemia-reperfusion injury model for studying blood-brain barrier dysfunction. J. Vis. Exp., 99:e52699.
Cengiz, P. et al. (2011) Inhibition of Na+/H+ exchanger isoform 1 is neuroprotective in neonatal hypoxic ischemic brain injury. Antioxid. Redox. Signal. 14: 1803-1813.
Chanana, V. et al. (2016) Sex Differences in Mouse Hippocampal Astrocytes after In-Vitro Ischemia. J. Vis. Exp. 116.
Cheng, Y. et al. (2010) MicroRNA-21 in cardiovascular disease. J. Cardiovasc. Transl. Res., 3: 251-255.
Cikla, U. et al. (2016) ERα Signaling Is Required forTrkB-Mediated Hippocampal Neuroprotection in Female Neonatal Mice after Hypoxic Ischemic Encephalopathy (1,2,3). eNeuro. 3: 1-14.
Da Costa Martins, PA et al. (2012) MicroRNAs in control of cardiac hypertrophy. Cardiovasc. Res., 93: 563-572.
Fichtlscherer, S. et al. (2011) Circulating microRNAs: biomarkers or mediators of cardiovascular diseases? Arterioscler. Thromb. Vasc. Biol., 31: 2383-2390.
Griffiths-Jones, S. (2004) The microRNA Registry. Nucleic Acids Research. 32: D109-D111.
Griffiths-Jones, S. et al. (2008) MiRbase: tools for microRNA genomics. Nucleic Acids Research. 36: D154-D158.
Griffiths-Jones, S. et al. (2006) MiRbase: microRNA sequences, targets and gene nomenclature. Nucleic Acids Research. 34: D140-D144.
Guo, F. et al. (2013) A novel domain of amino-Nogo-A protects HT22 cells exposed to oxygen glucose deprivation by inhibiting NADPH oxidase activity. Cell. Mol. Neurobiol., 33:443-452.
He, W. et al. (2016) Bioinformatic Analysis of Potential microRNAs in Ischemic Stroke. J. Stroke. Cerebrovasc. Dis., 25: 1753-1759.
Huang, D.W. et al. (2009) Systematic and integrative analysis of large gene lists using DAVID Bioinformatics Resources. Nature. Protoc., 4: 44-57.

(Continued)

Primary Examiner — Brian Whiteman
(74) Attorney, Agent, or Firm — Edwin S. Flores; Daniel J. Chalker; Chalker Flores, LLP

(57) ABSTRACT

The present invention includes methods for detecting and reducing or inhibiting ischemic stroke in a mammal, the method comprising: (a) selecting microRNAs to downregulate selected from the group consisting of hsa-miR-96-5p, hsa-miR-99a-5p, hsa-miR-122-5p, hsa-miR-186-5p, hsa-miR-211-5p, hsa-mir-760, PC-3p-57664, or PC-5p-12969, (b) selecting microRNAs to upregulate selected from the group consisting of ggo-miR-139, hsa-miR-30d-5p, hsa-miR-22-3p, hsa-miR-23a-3p, mmu-miR-5124a, mmu-mir-6240-5p, PC-3p-32463, or PC-5p-211, and combinations thereof, and (c) administering an agent that: downregulates that targets in (a), upregulates the targets in (b), or both, to the subject in an amount sufficient to reduce or inhibit ischemic stroke in the mammal. The present invention also includes the detection of the markers for use with stroke patients.

14 Claims, 17 Drawing Sheets

Specification includes a Sequence Listing.

(56) References Cited

OTHER PUBLICATIONS

Jickling, G.C. et al. (2014) MicroRNA expression in peripheral blood cells following acute ischemic stroke and their predicted gene targets. PLoS One. 9: e99283.

Jung, H.J. et al. (2014) Circulating miRNAs in aging and age related disease. J. Genet. Genom., 41: 465-472.

Koutsis, G. et al. (2013) The emerging role of microRNA in stroke. Curr. Top. Med. Chem., 13: 1573-1588.

Kumar, S. et al. (2017) MicroRNA-455-3p as a potential peripheral biomarker for Alzheimer's disease. Hum. Mol. Genet., 26: 3808-3822.

Laterza, O.F. et al. (2009) Plasma MicroRNAs as sensitive and specific biomarkers of tissue injury. Clin. Chem., 55:1977-83.

Lee, J.E. et al. (2011) MicroRNA signatures associated with immortalization of EBV-transformed lymphoblastoid cell lines and their clinical traits. Cell. Prolif., 44: 59-66.

Lewis, B.P. et al. (2005) Conserved seed pairing, often flanked by adenosines, indicates that thousands of human genes are microRNA targets. Cell. 120: 15-20.

Liu da, Z. et al. (2016) Elevating microRNA-122 in blood improves outcomes after temporary middle cerebral artery occlusion in rats. J. Cereb. Blood. Flow. Metab., 36: 1374-1383.

Livak, K.J. et al. (2001) Analysis of relative gene expression data using real-time quantitative PCR and the 2-$\Delta\Delta CT$ method. Methods. 25: 402-108.

Long, G. et al. (2013) Circulating miR-30a, miR-126 and let-7b as biomarker for ischemic stroke in humans. BMC. Neurol., 13: 178.

Lorenzen, J.M. et al. (2012) Circulating and urinary microRNAs in kidney disease. Clin. J. Am. Soc. Nephrol., 7: 1528-1533.

Lozano, R. et al. (2012) Global and regional mortality from 235 causes of death for 20 age groups in 1990 and 2010: a systematic analysis for the Global Burden of Disease Study 2010. Lancet, 380: 2095-2128.

Martinez, B. et al. (2016) Blood microRNAs as potential diagnostic and prognostic markers in cerebral ischemic injury. Neural. Regen. Res. 11: 1375-1378.

Murray, C.J et al. (2012) Disability-adjusted life years (DALYs) for 291 diseases and injuries in 21 regions, 1990-2010: a systematic analysis for the Global Burden of Disease Study 2010, Lancet, 380: 2197-2223.

Nieto-Diaz, M et al. (2014) MicroRNA dysregulation in spinal cord injury: causes, consequences and therapeutics. Front. Cell. Neurosci., 8: 53.

Ouyang, Y.B. et al. (2013) MicroRNAs: innovative targets for cerebral ischemia and stroke. Curr. Drug. Targets., 14: 90.

Pendlebury, S.T et al. (2009) Prevalence, incidence, and factors associated with pre-stroke and post-stroke dementia: a systematic review and meta-analysis. Lancet Neurol., 8:1006-1018.

Rosamond, W., et al. (2008) American Heart Association Statistics Committee and Stroke Statistics Subcommittee. Heart disease and stroke statistics—2008 update: a report from the American Heart Association Statistics Committee and Stroke Statistics Subcommittee Circulation, 117: e25-e146.

Schmitt, A. et al. (2008) Is brain banking of psychiatric cases valuable for neurobiological research? Clinics (Sao Paulo). 63: 255-266.

Schwarzenbach, H. et al. (2014) Clinical relevance of circulating cell-free microRNAs in cancer. Nat. Rev. Clin. Oncol., 11: 145-156.

Sepramaniam, S. et al. (2014) Circulating microRNAs as biomarkers of acute stroke. Int. J. Mol. Sci., 15: 1418-1432.

Siegel, C. et al. (2011) miR-23a regulation of X-linked inhibitor of apoptosis (XIAP) contributes to sex differences in the response to cerebral ischemia. Proc. Natl. Acad. Sci. U S A., 108: 11662-11667.

Stanzione, R. et al. (2017) A decrease of brain microRNA-122 level is an early marker of cerebrovascular disease in the stroke-prone spontaneously hypertensive rat. Oxid. Med. Cell. Longev., 2017:1206420.

Tan, L. et al. (2014) Circulating miR-125b as a biomarker of Alzheimer's disease. J. Neurol. Sci., 336: 52-56.

Uluc, K. et al. (2013) TrkB receptor agonist 7, 8 dihydroxyflavone triggers profound gender- dependent neuroprotection in mice after perinatal hypoxia and ischemia. CNS. Neurol. Disord. Drug. Targets. 12: 360-370.

Vannucci, R.C. et al. (1997) A model of perinatal hypoxic-ischemic brain damage. Ann. N. Y. Acad. Sci., 835: 234-249.

Vijayan, M. et al. (2016) Peripheral biomarkers of stroke: Focus on circulatory microRNAs. Biochim. Biophys. Acta., 1862:1984-1993.

Wang, W. et al. (2014) Circulating microRNAs as novel potential biomarkers for early diagnosis of acute stroke in humans. J. Stroke. Cerebrovasc. Dis., 23: 2607-2613.

Wheeler, H.E. et al. (2012) Lymphoblastoid cell lines in pharmacogenomic discovery and clinical translation. Pharmacogenomics. 13: 55-70.

Yu, Z. et al. (2009) Neuroglobin-overexpression alters hypoxic response gene expression in primary neuron culture following oxygen glucose deprivation. Neuroscience. 162: 396-403.

Yuan, Y. et al. (2016) Crosstalk between miRNAs and their regulated genes network in stroke. Sci. Rep., 6: 20429.

Zhao, H. et al. (2017) MicroRNA-99a-5p in circulating immune cells as a potential biomarker for the early diagnosis of ischemic stroke. Brain. Circ., 3:21-28.

Zhu, H. et al. (2012) Baicalin reduces the permeability of the blood-brain barrier during hypoxia in vitro by increasing the expression of tight junction proteins in brain microvascular endothelial cells. J. Ethnopharmacol., 141: 714-720.

Ziu, M. et al. (2011) Temporal differences in microRNA expression patterns in astrocytes and neurons after ischemic injury. PLoS One. 6: e14724.

\* cited by examiner

MICRORNAS AS THERAPEUTIC TARGETS FOR ISCHEMIC STROKE

CROSS-REFERENCE TO RELATED APPLICATIONS

This application claims priority to and is the National Stage of International Application No. PCT/US2019/028069, filed on Apr. 18, 2019 and claims priority to U.S. Provisional Application Ser. No. 62/660,649, filed Apr. 20, 2018, the entire contents of which are incorporated herein by reference.

STATEMENT OF FEDERALLY FUNDED RESEARCH

This invention was made with government support under AG042178, AG47812 and NS105473, K08 NS088563, and P30 HD03352 awarded by the National Institutes of Health, National Institute of Neurological Disorders and Stroke. The government has certain rights in the invention.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Apr. 16, 2019, is named TECH2119WO_SeqList.txt and is 2 kilobytes in size.

TECHNICAL FIELD OF THE INVENTION

The present invention relates in general to the field of therapeutic targets and peripheral biomarkers for ischemic stroke.

BACKGROUND OF THE INVENTION

Without limiting the scope of the invention, its background is described in connection with stroke.

Stroke is the third leading cause of death in the United States and the leading cause of serious, long-term disability. Stroke is a condition in which impeded blood flow to the brain results in cellular death. There are two main types of stroke: hemorrhagic, due to bleeding and trauma, and ischemic, due to a lack of blood flow. The disclosed technology will focus on the ischemic form of stroke. Currently, the preferred method of diagnosing ischemic stroke used radiographic imaging. While this method is quick and accurate, it is extremely expensive and the availability of diagnostic imaging equipment will vary among clinics and hospitals.

One such patent is U.S. Pat. No. 8,956,817, issued to Goel, entitled "Identification of microRNAs (miRNAs) in fecal samples as biomarkers for gastroenterological cancers". This inventor teaches detection of miRNA-based biomarkers in human stool specimens, by amplifying miRNA directly from stool specimens without any prior miRNA extraction. Differential expression of specific microRNAs in stool of colorectal cancer CRC and adenoma patients using fecal microRNAs is said to be a novel biomarker for colorectal neoplasia detection.

Another such patent is Chinese Patent Application No. CN103667445A, filed by Lei and Wanhua, and entitled "Marker for early diagnosis of cerebral infarction and application thereof". These applicants are said to teach a marker for early diagnosis of cerebral infarction composed of multiple nucleic acid molecules, that is at least one microRNA (ribonucleic acid) sequence encoding any one of hsa-miR-106B-5P, hsa-miR-4306, hsa-miR-320e and hsa-miR-320d.

Finally, Wanhua and Zeng, in an article entitled "Circulating MicroRNAa as Novel Potential Biomarkers for Early Diagnosis of Acute Stroke in Humans" J. of Stroke and Cerebrovascular Disease, November 2014, teach the discovery of circulating miRNAs as a biomarker for disease.

However, a need remains for novel targets and treatments for ischemic stroke based on the targeting of peripheral biomarkers of ischemic stroke.

SUMMARY OF THE INVENTION

In one embodiment, the present invention includes a method to reduce or inhibit ischemic stroke in a mammal, the method comprising: (a) selecting microRNAs to downregulate selected from the group consisting of hsa-miR-96-5p, hsa-miR-99a-5p, hsa-miR-122-5p, hsa-miR-186-5p, hsa-miR-211-5p, hsa-mir-760, PC-3p-57664, or PC-5p-12969; (b) selecting microRNAs to upregulate selected from the group consisting of ggo-miR-139, hsa-miR-30d-5p, hsa-miR-22-3p, hsa-miR-23a-3p, mmu-miR-5124a, mmu-mir-6240-5p, PC-3p-32463, or PC-5p-211, and combinations thereof; and (c) administering one or more agent that: downregulates the microRNAs in (a), upregulates the microRNAs in (b), or both, to the mammal in an amount sufficient to reduce or inhibit ischemic stroke in the mammal. In one aspect, the mammal is a human. In another aspect, the one or more agents is selected from an oligonucleotide that modified the expression of the one or more microRNA. In another aspect, the at least one or more oligonucleotides contains a non-naturally occurring modification comprising modifications or substitutions of: (1) the ribose or other sugar units, (2) bases, or (3) the backbone, selected from: one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions, partially or completely modified backbones, such as fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, sugar modifications such as 2'-O-methyl (2'-O-methylnucleotides), 2'-O-methyloxyethoxy (2'-O-MOE), a 2'-O-alkyl modified sugar moiety, or a bicyclic sugar moiety, nucleotide mimetics, peptide nucleic acids (PNA), morpholino nucleic acids, cyclohexenyl nucleic acids, anhydrohexitol nucleic acids, glycol nucleic acid, threose nucleic acid, and locked nucleic acids (LNA), and a combinations of two or more of any of the foregoing. In another aspect, the oligonucleotide is selected from any of hsa-miR-96-5p, hsa-miR-99a-5p, hsa-miR-122-5p, hsa-miR-186-5p, hsa-miR-211-5p, hsa-mir-760, PC-3p-57664, or PC-5p-12969, ggo-miR-139, hsa-miR-30d-5p, hsa-miR-22-3p, hsa-miR-23a-3p, mmu-miR-5124a, mmu-mir-6240-5p, PC-3p-

32463, or PC-5p-211, or a sequence having at least 88, 92, 93, 94, 95, 96, 97, 98, or 99% identity with those sequences. In another aspect, the oligonucleotide targets one or more regulatory regions that downregulate or upregulate messenger RNA transcription. In another aspect, a profile of (a) or (b) is used to differentiate between hypoxia and ischemia. In another aspect, the method further comprises the steps of treating the patient for ischemic stroke and measuring the levels the miRNAs for PC-3p-57664, PC-5p-12969, hsa-miR-122-5p and hsa-miR-211-5p to determine if they were downregulated as a result of the treatment, or the measuring the levels the miRNAs for PC-3p-32463, PC-5p-211, ggo-miR-139, hsa-miR-30d-5p, mmu-mir-6240-p5, hsa-miR-23a-3p to determine if they were upregulated a result of the treatment, or both. In another aspect, the one or more agent further comprises a pharmaceutically acceptable excipient, salts, or carrier. In another aspect, the one or more agents is/are adapted for intravenous, intramuscular, intraperitoneal, oral, subcutaneous, enteral or parenteral administration. In another aspect, the microRNAs targeted consist of PC-3p-57664, PC-5p-12969, miR-30a, and miR-30d. In another aspect, the microRNAs targeted consist of miR-122-5p, and miR-211-5p, PC-3p-57664, and PC-5p-12969.

In another embodiment, the present invention includes a method to reduce or inhibit ischemic damage in a mammal, the method comprising: (a) selecting microRNAs to downregulate selected from the group consisting of hsa-miR-96-5p, hsa-miR-99a-5p, hsa-miR-122-5p, hsa-miR-186-5p, hsa-miR-211-5p, hsa-mir-760, PC-3p-57664, or PC-5p-12969; (b) selecting microRNAs to upregulate selected from the group consisting of ggo-miR-139, hsa-miR-30d-5p, hsa-miR-22-3p, hsa-miR-23a-3p, mmu-miR-5124a, mmu-mir-6240-5p, PC-3p-32463, or PC-5p-211, and combinations thereof; and (c) administering one or more agents that modify the expression of microRNA in (a), (b), or both, to the mammal with ischemic damage. In one aspect, the mammal is a human. In another aspect, the one or more agents is/are selected from an oligonucleotide that modified the expression of the one or more microRNA. In another aspect, the at least one or more oligonucleotides contains a non-naturally occurring modification comprising modifications or substitutions of: (1) the ribose or other sugar units, (2) bases, or (3) the backbone, selected from: one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions, partially or completely modified backbones, such as fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, sugar modifications such as 2'-O-methyl (2'-O-methylnucleotides), 2'-O-methyloxyethoxy (2'-O-MOE), a 2'-O-alkyl modified sugar moiety, or a bicyclic sugar moiety, nucleotide mimetics, peptide nucleic acids (PNA), morpholino nucleic acids, cyclohexenyl nucleic acids, anhydrohexitol nucleic acids, glycol nucleic acid, threose nucleic acid, and locked nucleic acids (LNA), and a combinations of two or more of any of the foregoing. In another aspect, the oligonucleotide is selected from any of hsa-miR-96-5p, hsa-miR-99a-5p, hsa-miR-122-5p, hsa-miR-186-5p, hsa-miR-211-5p, hsa-mir-760, PC-3p-57664, or PC-5p-12969, ggo-miR-139, hsa-miR-30d-5p, hsa-miR-22-3p, hsa-miR-23a-3p, mmu-miR-5124a, mmu-mir-6240-5p, PC-3p-32463, or PC-5p-211, or a sequence having at least 88, 92, 93, 94, 95, 96, 97, 98, or 99% identity with those sequences. In another aspect, the oligonucleotide targets one or more regulatory regions that downregulate or upregulate messenger RNA transcription. In another aspect, a profile of (a) or (b) is used to differentiate between hypoxia and ischemia. In another aspect, the method further comprises the steps of treating the patient for ischemic stroke and measuring the levels the miRNAs for PC-3p-57664, PC-5p-12969, hsa-miR-122-5p and hsa-miR-211-5p to determine if they were downregulated as a result of the treatment, or the measuring the levels the miRNAs for PC-3p-32463, PC-5p-211, ggo-miR-139, hsa-miR-30d-5p, mmu-mir-6240-p5, hsa-miR-23a-3p to determine if they were upregulated a result of the treatment, or both. In another aspect, the one or more agents further comprises a pharmaceutically acceptable excipient, salts, or carrier. In another aspect, the one or more agents is adapted for intravenous, intramuscular, intraperitoneal, oral, subcutaneous, enteral or parenteral administration. In another aspect, the microRNAs targeted consist of PC-3p-57664, PC-5p-12969, miR-30a, and miR-30d. In another aspect, the microRNAs targeted consist of miR-122-5p, miR-211-5p, PC-3p-57664, and PC-5p-12969.

In yet another embodiment, the present invention includes a method of detecting microRNAs from a subject, the method comprising: (a) measuring in a blood sample the level of microRNAs selected from the group consisting of hsa-miR-96-5p, hsa-miR-99a-5p, hsa-miR-122-5p, hsa-miR-186-5p, hsa-miR-211-5p, hsa-mir-760, PC-3p-57664, or PC-5p-12969; or (b) measuring in a blood sample the level of microRNAs selected from the group consisting of ggo-miR-139, hsa-miR-30d-5p, hsa-miR-22-3p, hsa-miR-23a-3p, mmu-miR-5124a, mmu-mir-6240-5p, PC-3p-32463, or PC-5p-211, and combinations thereof; (c) determining if: the level of microRNAs in (a) is upregulated when compared to normal samples; the level of microRNAs in (b) is downregulated when compared to normal samples; and (d) displaying the results for (a) and (b). In one aspect, the method further comprises the step of selecting between a treatment for hypoxia or ischemia depending on the results displayed in (d).

In another embodiment, the present invention includes a method of diagnosing a subject with a stroke, the method comprising: (a) measuring in a blood sample the level of microRNAs selected from the group consisting of hsa-miR-96-5p, hsa-miR-99a-5p, hsa-miR-122-5p, hsa-miR-186-5p, hsa-miR-211-5p, hsa-mir-760, PC-3p-57664, or PC-5p-12969; or (b) measuring in a blood sample the level of microRNAs selected from the group consisting of ggo-miR-139, hsa-miR-30d-5p, hsa-miR-22-3p, hsa-miR-23a-3p, mmu-miR-5124a, mmu-mir-6240-5p, PC-3p-32463, or PC-5p-211, and combinations thereof; (c) determining if: the level of one or more microRNAs in (a) is upregulated when compared to normal samples; the level of one or more microRNAs in (b) is downregulated when compared to normal samples, or both, wherein the presence of (a), (b), or both is indicative that the subject had a stroke.

BRIEF DESCRIPTION OF THE DRAWINGS

For a more complete understanding of the features and advantages of the present invention, reference is now made to the detailed description of the invention along with the accompanying figures and in which:

(FIG. 3A) MicroRNAs expression in OGD/R treated human neuroblastoma cells (SH-SY5Y) by qRT-PCR. Data are presented as the mean±SD of three independent experiments, and (FIG. 3B) MicroRNAs expression in OGD/R treated mouse neuroblastoma cells (N2a) by qRT-PCR.

FIG. 5A Serum, FIG. 5B postmortem IS brains, FIG. 5C IS lymphoblastoid IS cell lines, and FIG. 5D HI stroke mouse model (Hippocampus).

FIG. 7A Normal Control Cells, FIG. 7B Cells+Agomir, FIG. 7C Cells+Antagomir, FIG. 7D OGD treated Cells, FIG. 7E Cells+Agomir+OGD, and FIG. 7F Cells+Antagomir+OGD.

DETAILED DESCRIPTION OF THE INVENTION

Figure 1:
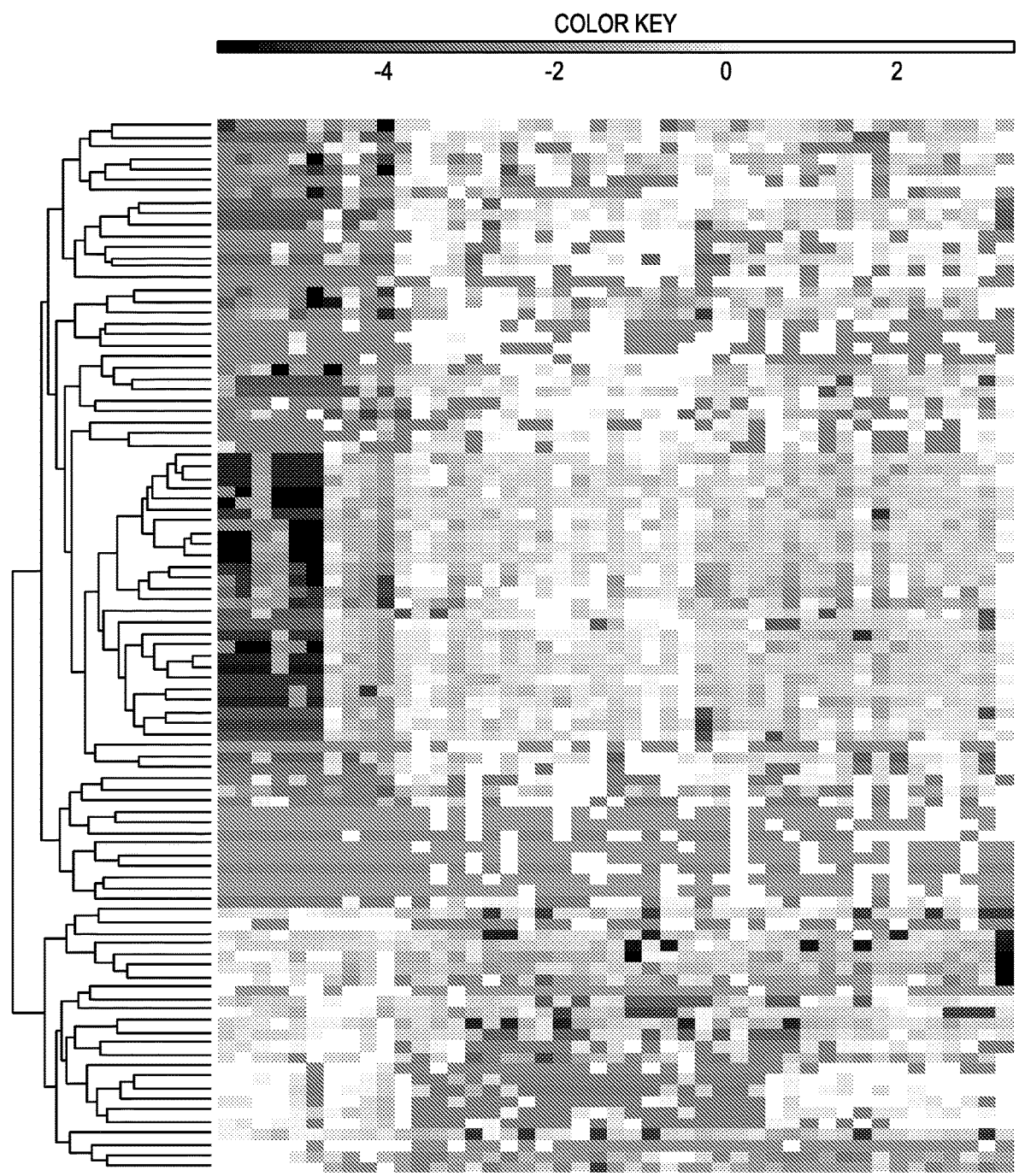
FIG. 1 is a heat map of the hierarchical cluster analysis of differentially expressed miRNAs between ischemic stroke patients and healthy controls detected by deep Sequencing. The color indicates the log 2-fold change from high (red) to low (green), as indicated by the color key.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, organic synthesis, nucleic acid chemistry and nucleic acid hybridization are those well known and commonly employed in the art. Further, standard techniques can be used for nucleic acid and peptide synthesis. Such techniques and procedures are generally performed according to conventional methods known in the art and from various general references (e.g., Sambrook and Russell, 2012, Molecular Cloning, A Laboratory Approach, Cold Spring Harbor Press, Cold Spring Harbor, N.Y., and Ausubel et al., 2012, Current Protocols in Molecular Biology, John Wiley & Sons, NY), relevant portions incorporated herein by reference.

Conventional notations are used herein to describe polynucleotide sequences, e.g., the left-hand end of a single-stranded polynucleotide sequence is the 5'-end and vice versa for the 3'-end (right-hand end); the left-hand direction of a double-stranded polynucleotide sequence is referred to as the 5'-direction and vice versa for the 3'-direction (right-hand direction), with regard to sequences, such as those that become coding sequences. The direction of 5' to 3' addition of nucleotides to nascent RNA transcripts is referred to as the transcription direction. The DNA strand having the same sequence as an mRNA is referred to as the "coding strand". Sequences on the DNA or RNA strand that are located 5' to a reference point on the DNA or RNA are referred to as "upstream sequences", and sequences on the DNA or RNA strand that are 3' to a reference point on the DNA or RNA are referred to as "downstream sequences."

As used herein, the term "antisense" refers to an oligonucleotide having a sequence that hybridizes to a target sequence in RNA by Watson-Crick base pairing, to form an RNA:oligonucleotide heteroduplex with the target sequence, typically with an mRNA or pre-mRNA. The antisense oligonucleotide may have exact sequence complementarity to the target sequence or near complementarity. These antisense oligonucleotides may block or inhibit translation of the mRNA, and/or modify the processing of an mRNA to produce a splice variant of the mRNA. It is not necessary that the antisense sequence be complementary solely to the coding portion of the RNA molecule. The antisense sequence may be complementary to regulatory sequences specified on the non-coding region of an RNA molecule (e.g. introns, untranslated regions) encoding a protein, which regulatory sequences control expression of the coding sequences. Antisense oligonucleotides are typically between about 5 to about 100 nucleotides in length, more typically, between about 7 and about 50 nucleotides in length, and even more typically between about 10 nucleotides and about 30 nucleotides in length.

As used herein, the term "nucleic acid" or a "nucleic acid molecule" refer to any DNA or RNA molecule, either single or double stranded, whether in linear or circular form. With reference to nucleic acids of the present invention, the term "isolated nucleic acid", when applied to DNA or RNA, refers to a DNA or RNA molecule that is separated from sequences with which it is immediately contiguous in the naturally occurring genome or gene products of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

As used herein, the terms "specifically hybridizing" or "substantially complementary" refer to the association between two nucleotide molecules of sufficient complementarity to permit hybridization under pre-determined conditions generally used in the art. Examples of low, middle or intermediate and high stringency hybridization conditions are well known to the skilled artisan, e.g., using Sambrook and Russell, 2012, Molecular Cloning, A Laboratory Approach, Cold Spring Harbor Press, Cold Spring Harbor, N.Y., or Ausubel et al., 2012, Current Protocols in Molecular Biology, John Wiley & Sons, NY, relevant portions incorporated herein by reference.

As used herein, the phrase "chemically modified oligonucleotide" refers to a short nucleic acid (DNA or RNA) that can be a sense or antisense that includes modifications or substitutions of: (1) the ribose or other sugar units, (2) bases, or (3) the backbone, which in nature is composed of phosphates, as are known in the art. Non-limiting examples of modifications or nucleotide analogs include, without limitation, nucleotides with phosphate modifications comprising one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions (see, e.g., Hunziker and Leumann (1995) Nucleic Acid Analogues: Synthesis and Properties, in Modern Synthetic Methods, VCH, 331-417; Mesmaeker et al. (1994) Novel Backbone Replacements for Oligonucleotides, in Carbohydrate Modifications in Antisense Research, ACS, 24-39); nucleotides with modified sugars (see, e.g., U.S. Patent Application Publication No. 2005/0118605) and sugar modifications such as 2'-O-methyl (2'-O-methylnucleotides) and 2'-O-methyloxyethoxy (2'-O-MOE), a 2'-O-alkyl modified sugar moiety, or a bicyclic sugar moiety, and nucleotide mimetics such as, without limitation, peptide nucleic acids (PNA), morpholino nucleic acids, cyclohexenyl nucleic acids, anhydrohexitol nucleic acids, glycol nucleic acid, threose nucleic acid, and locked nucleic acids (LNA), as well as partially or completely modified backbones, such as fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, and a combinations of two or more of any of the foregoing (see, e.g., U.S. Pat. Nos. 5,886,165; 6,140,482; 5,693,773; 5,856,462; 5,973,136; 5,929,226; 6,194,598; 6,172,209; 6,175,004; 6,166,197; 6,166,188; 6,160,152; 6,160,109; 6,153,737; 6,147,200; 6,146,829; 6,127,533; and 6,124,445, relevant portions incorporated herein by reference).

As used herein, the term "expression cassette" refers to a nucleic acid molecule comprising a coding sequence operably linked to promoter/regulatory sequences necessary for transcription, processing and, optionally, translation or splicing of the coding sequence.

As used herein, the term "promoter/regulatory sequence" refers to a nucleic acid sequence that is required for expression of a gene product operably linked to the promoter/regulator sequence. In some instances, the promoter/regulatory sequence may be the core promoter sequence and in other instances, this sequence may also include an enhancer sequence and other regulatory elements that are required for expression of the gene product. The promoter/regulatory sequence may be, for example, a sequence that drives the expression of a gene product in a constitutive and/or inducible manner.

As used herein, the term "inducible promoter" refers to a nucleotide sequence which, when operably linked with a polynucleotide which encodes or specifies a gene product, causes the gene product to be produced substantially only when an inducer which corresponds to the promoter is present.

As used herein, the terms "percent similarity", "percent identity" and "percent homology", when referring to a comparison between two specific sequences, identify the percentage or bases that are the same along a particular sequence. The percentage of similarity, identify or homology can be calculated using, e.g., the University of Wisconsin GCG software program or equivalents.

As used herein, the term "oligonucleotide," refers to a nucleic acid strand, single or double stranded that has a length that is, typically, less than a coding sequence for a gene, e.g., the oligonucleotide will generally be at least 4-6 bases or base-pairs in length, and up to about 200, with the most typical oligonucleotide being in the range of 8-20, 10-25, 12-30, or about 30, 35, 40, or 50 bases or base-pairs. The exact size of the oligonucleotide will depend on various factors and on the particular application and use of the oligonucleotide, which can be varied as will be known to the skilled artisan without undue experimentation following the teachings herein and as taught in, e.g., Sambrook and Russell, 2012, Molecular Cloning, A Laboratory Approach, Cold Spring Harbor Press, Cold Spring Harbor, N.Y., or Ausubel et al., 2012, Current Protocols in Molecular Biology, John Wiley & Sons, NY, relevant portions incorporated herein by reference.

As used herein, the term "treatment", refers to reversing, alleviating, delaying the onset of, inhibiting the progress of, and/or preventing a disease or disorder, or one or more symptoms thereof, to which the term is applied in a subject, e.g., ischemic stroke. In some embodiments, the treatment may be applied after one or more symptoms have developed. In other embodiments, treatment may be administered in the absence of symptoms. For example, treatment may be administered prior to symptoms (e.g., in light of a history of symptoms and/or one or more other susceptibility factors), or after symptoms have resolved, for example to prevent or delay their reoccurrence.

As used herein, the terms "effective amount" and "pharmaceutically effective amount" refer to a sufficient amount of an agent to provide the desired biological result. Preferably, the sufficient amount of the agent does not induce toxic side effects. The present invention should lead to a reduction and/or alleviation of the signs, symptoms, or causes of ischemic stroke. An appropriate effective amount in any individual case may be determined by one of ordinary skill in the art using routine experimentation.

The present invention may be provided in conjunction with one or more "pharmaceutically acceptable" agents, carriers, buffers, salts, or other agents listed in the U.S. Pharmacopeia or other generally recognized pharmacopeia for use in animals, and more particularly in humans, which generally indicates approval by a regulatory agency of the Federal government or a state government. Typical pharmaceutically acceptable formulations for use with oligonucleotides include but are not limited to salts such as: calcium chloride dihydrate (US Pharmacopeia (USP)), magnesium chloride hexahydrate USP, potassium chloride USP, sodium chloride USP; and may include buffers such as" sodium phosphate dibasic anhydrous USP, sodium phosphate monobasic dihydrate USP, and water USP. Typically, the pH of the product may be modified using hydrochloric acid or sodium hydroxide to a pH of −6.8, 6.9, 7.0, 7.1, or 7.2.

MicroRNAs (miRNAs) are involved in growth, development, and occurrence and progression of many diseases. MiRNA mediated post-transcriptional regulation is poorly understood in vascular biology and pathology. The purpose of our study is to determine circulatory miRNAs as early detectable peripheral biomarkers in patients with ischemic stroke (IS). MiRNAs expression levels were measured in IS serum samples and healthy controls using Illumina deep sequencing analysis and identified differentially expressed miRNAs. Differentially expressed miRNAs were further validated using SYBR-green based quantitative real-time PCR assay (qRT-PCR) in postmortem IS brains, lymphoblastoid IS cell lines, OGD/R treated human and mouse neuroblastoma cells, and mouse models of hypoxia and ischemia (HI) induced stroke. A total of 4,656 miRNAs were differentially expressed in IS serum samples relative to healthy controls. Out of 4,656 miRNAs, 272 were found to be significantly deregulated in IS patients. Interestingly, the inventors found several novel and previously unreported miRNAs in IS patients relative to healthy controls. Further analyses revealed that some candidate miRNAs and its target genes were involved in the regulation of the stroke. This is the first study identified potential novel candidate miRNAs in IS serum samples from the residents of rural West Texas. It is shown herein that the miRNAs identified in the present study can be used both as biomarkers and for targeted therapeutics for stroke.

Stroke is a common neurological disease with diverse etiologies that occurs when the blood supply to the brain is interrupted, resulting in a shortage of oxygen and nutrients to brain tissue. Due to multifactorial nature, stroke may be classified as a syndrome, not as a single disease. Stroke is the second leading cause of death globally and third leading cause of disability-adjusted life years worldwide (1, 2). An estimated 7.2 million Americans ≥20 years of age self-report having had a stroke and approximately 795000 strokes occur in the United States each year. On average, every 40 seconds, someone in the United States has a stroke, and on average, every 4 minutes, someone dies of a stroke. Prevalence of stroke in the United States increases with age in both men and women (3). Ischemic stroke (IS) is described as a lack of blood supply and oxygen availability to an area of the brain due to narrowed or blocked arteries leading to or within the brain and the most predominant type of stroke accounting for approximately 87% of stroke cases (4). Stroke doubles the risk for dementia (post-stroke dementia), and approximately 30% of stroke patients go on to develop cognitive dysfunction within 3 years (5, 6).

Biomarkers might be useful in identifying different diseases, such as stroke, cancer, diabetes, and disease severity (7, 8). Identification of biomarkers can inform researchers in their attempts to develop early detectable peripheral biomarkers and could contribute to a better understanding of the etiologies and mechanisms underlying particular diseases, such as stroke. Recent molecular biology discoveries have revealed that microRNAs (miRNAs) can detect changes in the bodily organs, including brain that may lead to IS. MiRNAs are important post-transcriptional regulators that connect with multiple target messenger RNAs coordinately regulating target genes. MiRNAs have also been found to be important regulators of leukocyte gene expression in acute IS cases (9). Many studies showed that miRNAs altered after central nervous system injury moderate processes that stimulate neuronal death with inflammation, apoptosis and oxidative stress (10, 11). Furthermore, miRNAs can act as sensitive biomarkers of secondary brain damage. Studies also suggested that peripheral blood miRNAs and their profiles could be developed as diagnostic and prognostic biomarkers of IS, as well as serving as innovative targets in the treatment of this disease (12). Clinical approaches accessible for the diagnosis and prognosis of stroke were restricted to radiological imaging, which was with limited availability and higher cost. Diagnosis of early stage of stroke and its development could be improved through the finding of new biomarkers. MiRNA mediated post-transcriptional regulation is poorly understood in vascular biology and pathology. However, there are no drugs/agents and peripheral biomarkers available that can delay and/or detect IS in humans. Hence, identification of blood-based early detectable miRNAs could contribute to a better understanding of the etiologies and mechanisms underlying IS.

The present inventors determined which miRNAs as early detectable biomarkers in serum samples from IS patients relative to healthy controls. The inventors used miRNA deep sequencing method and validated differentially expressed miRNAs using quantitative real-time PCR (qRT-PCR). Further, the inventors validated the selected miRNAs using postmortem IS brains, lymphoblastoid IS cell lines, oxygen and glucose deprivation/reoxygenation (OGD/R) treated human (SH-SY5Y) and mouse neuroblastoma (N2a) cells and hypoxia and ischemia (HI) induced stroke mouse model. Finally, the inventors demonstrate the results from targeting the biomarkers for the treatment of IS.

Example 1. miRNAs as Early Detectable Biomarkers in Serum Samples from Ischemia Patients Differentially expressed miRNA profile by deep sequencing. Illumina deep sequencing analysis of serum samples provided a total of 484,651,777 raw RNA reads. Among these, 341,678,616 (70.5%) were mapped to miRNAs, and 39,890,853 reads were mapped to mRNA and 24,723,087 reads were mapped to other RNAs (RFam: rRNA, tRNA, snRNA, snoRNA and others) (data not shown). Based on the size distribution of all known miRNAs, 15-32 nucleotide (nt) reads were selected as 'mappable reads' for further analysis (data not shown). Of these reads, 87.6% of the small RNAs were 17-22 nt in size, which is typical miRNA sizes produced by RNA Dicer-digested products. The mappable reads sequences were subjected to advance bioinformatics analysis and to simplify the data from sequencing, all identical sequence reads were grouped and then assigned a unique sequence tag (data not shown).

The miRNA sequencing analysis revealed/detected a total of 4,656 miRNAs in serum samples of IS patients versus healthy controls. Among them, 272 miRNAs were differentially deregulated (FC±2, P≤0.05) in IS patients, compared to healthy controls. Interestingly, 173 miRNAs were significantly upregulated, while 76 were found to be significantly down-regulated in IS patients.

Hierarchical clustering performed with differentially expressed miRNAs, revealed that miRNA expression patterns were able to classify individuals according to their disease status. Among these miRNAs, the inventors identified 16 miRNAs that were differentially expressed between the IS patients and healthy controls and where number of reads 10 in either IS patients or healthy controls were detected and at least a meaningful ±2-fold change between the group was identified (FIG. 1).

Figure 2A:
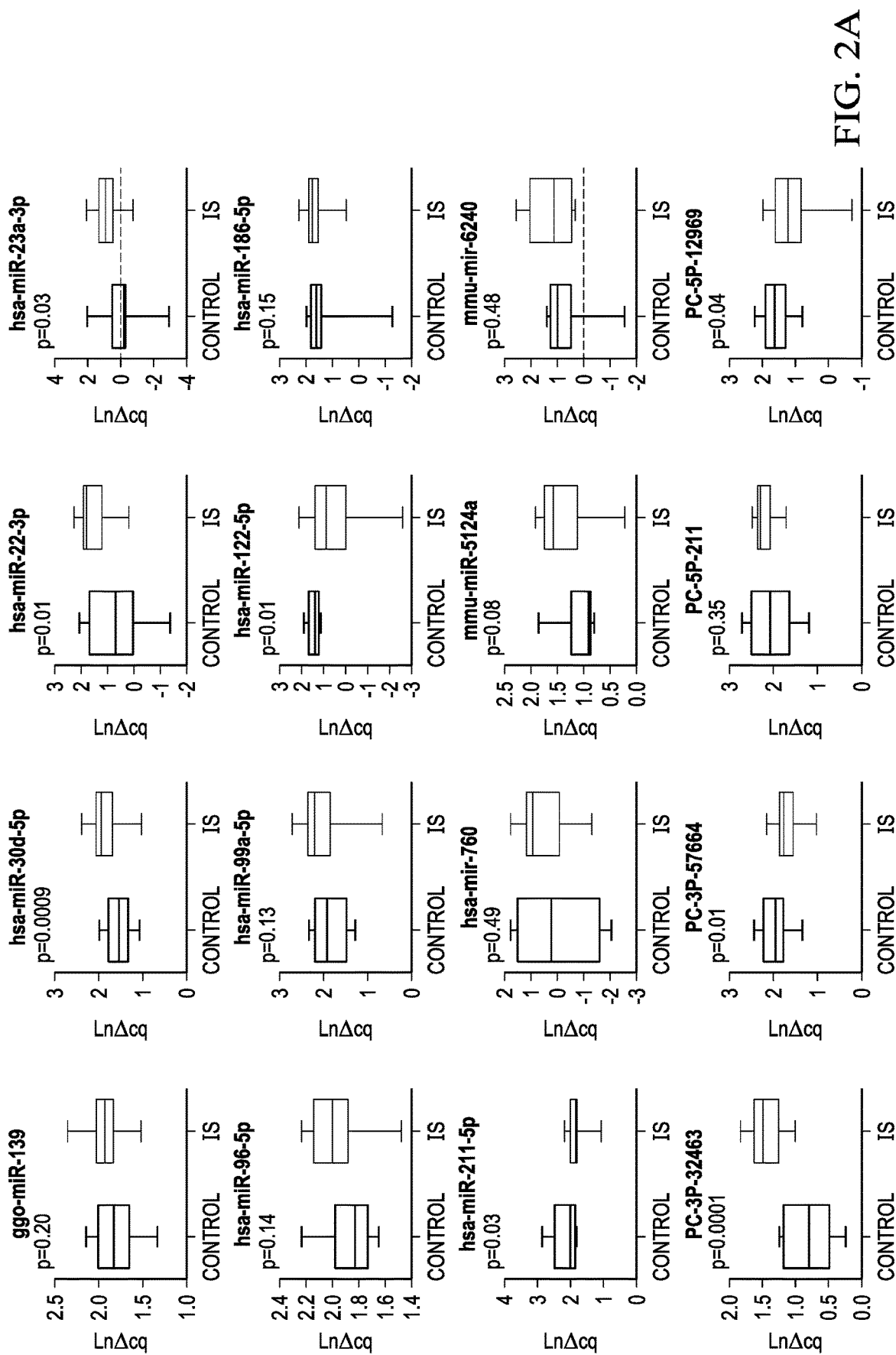
FIG. 2A shows the validation of candidate miRNAs in serum samples by qRT-PCR. Significantly deregulated miRNA expression in IS versus the healthy controls. The y-axis depicts LnΔCq. p-values were determined by Mann-Whitney test.

Validation of candidate miRNAs in serum samples by real-time RT-PCR. The inventors validated 16 miRNAs using real-time RT-PCR analysis in same RNA samples that were used for deep sequencing analysis. A few known and several novel and previously unreported miRNAs were found in IS serum samples. Of the 16 miRNAs differentially expressed between IS patients and healthy controls in the discovery cohort, the validation studies found that 4 miRNAs PC-3p-57664 (P=0.01), PC-5p-12969 (P=0.04), hsa-miR-122-5p (P=0.01), hsa-miR-211-5p (P=0.03) were significantly upregulated in IS patients compared with healthy controls. Whereas 4 miRNAs, hsa-miR-22-3p (P=0.01), PC-3p-32463 (P=0.0001), hsa-miR-30d-5p (P=0.0009), hsa-miR-23a-3p (P=0.03) were significantly down-regulated in the same comparison (FIG. 2A).

Figure 2B:
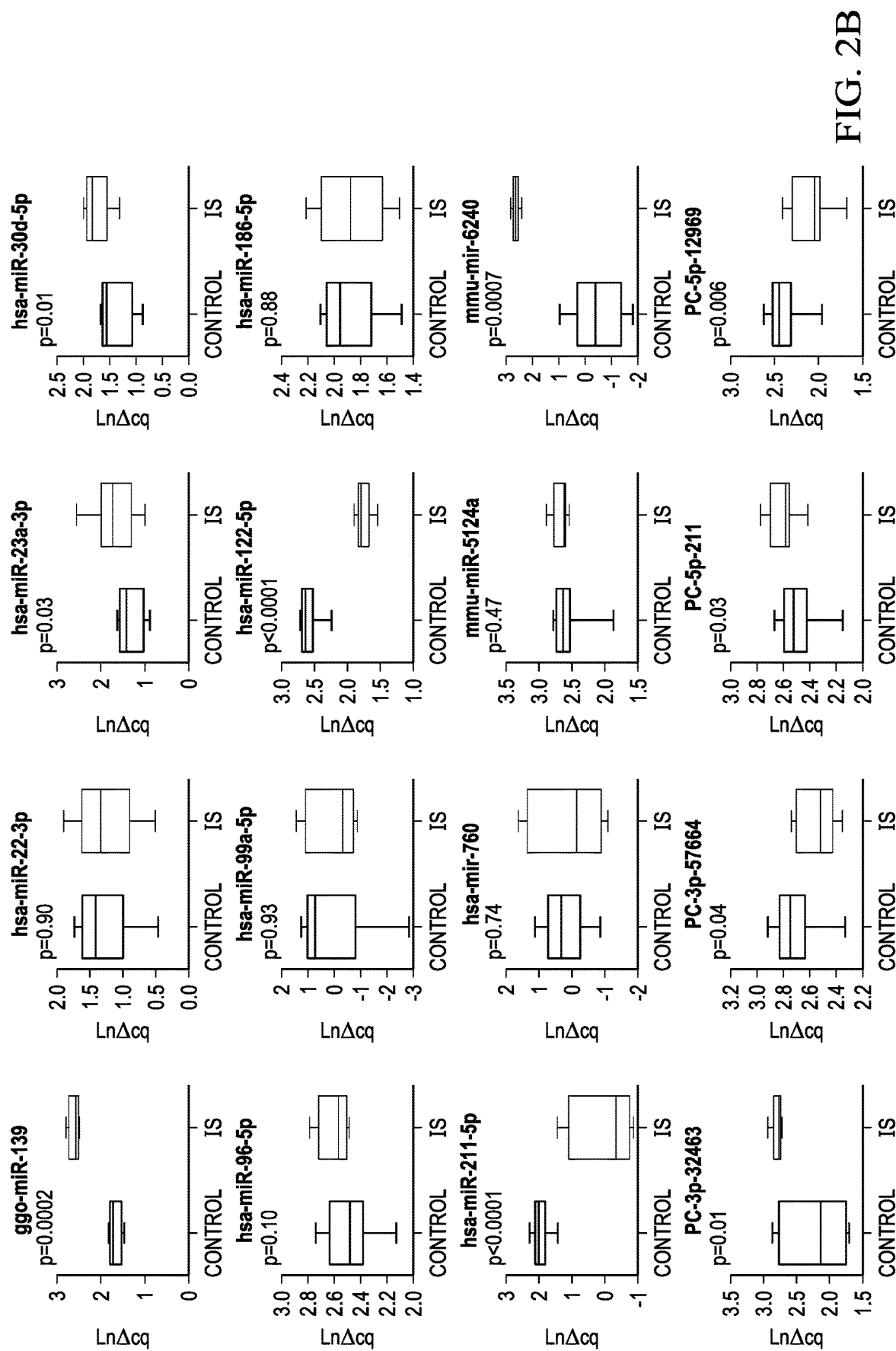
FIG. 2B shows the validation of serum miRNAs using postmortem IS brains by qRT-PCR. Box plots of LnΔCq values of significant serum miRNAs in IS brains compared to healthy control brains.

Validation of serum miRNAs using postmortem IS brains. The inventors analyzed the expression of above selected 16 miRNAs in the postmortem IS brains (n=10) and control brains (n=10) by real-time RT-PCR (data not shown). Analysis showed that, four miRNAs; PC-3p-57664 (P=0.04), PC-5p-12969 (P=0.006), hsa-miR-122-5p (P<0.0001) and hsa-miR-211-5p (P<0.0001) were consistently upregulated and three miRNAs, PC-3p-32463 (P=0.01), hsa-miR-30d-5p (P=0.01) and hsa-miR-23a-3p (P=0.03) were significantly down-regulated in the IS brains compared with control brains (FIG. 2B). The expression of PC-3p-57664, PC-5p-12969, hsa-miR-122-5p, hsa-miR-211-5p were the most significantly upregulated in both the IS serum and postmortem IS brains, suggesting that these upregulated miRNAs are relevant to IS—in terms of early detection and disease progression.

Figure 2C:
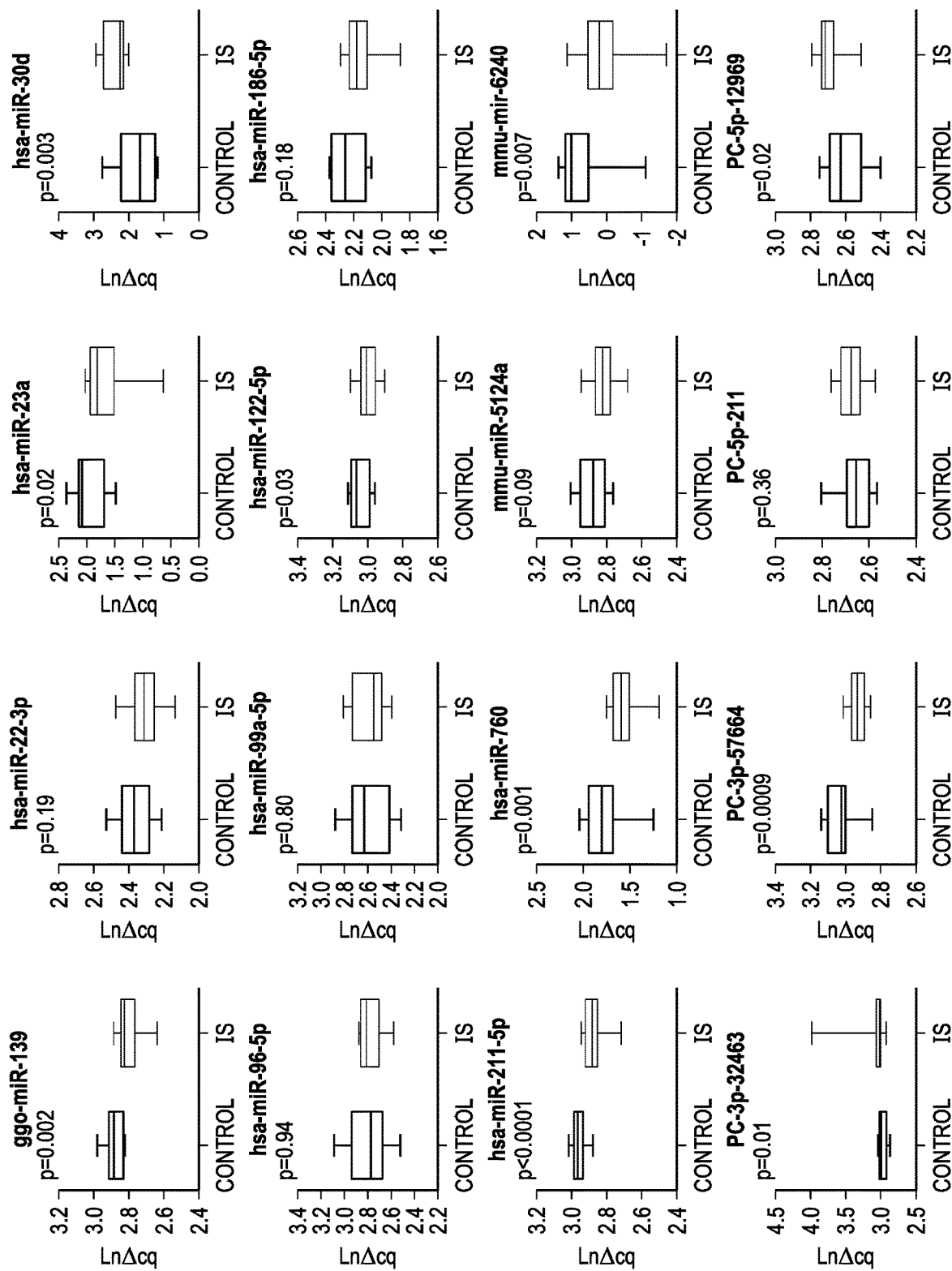
FIG. 2C shows the validation of the expression of 16 miRNAs identified from sequencing data employing lymphoblastoid IS cell lines and healthy control cell lines using qRT-PCR.
Figure 3A:
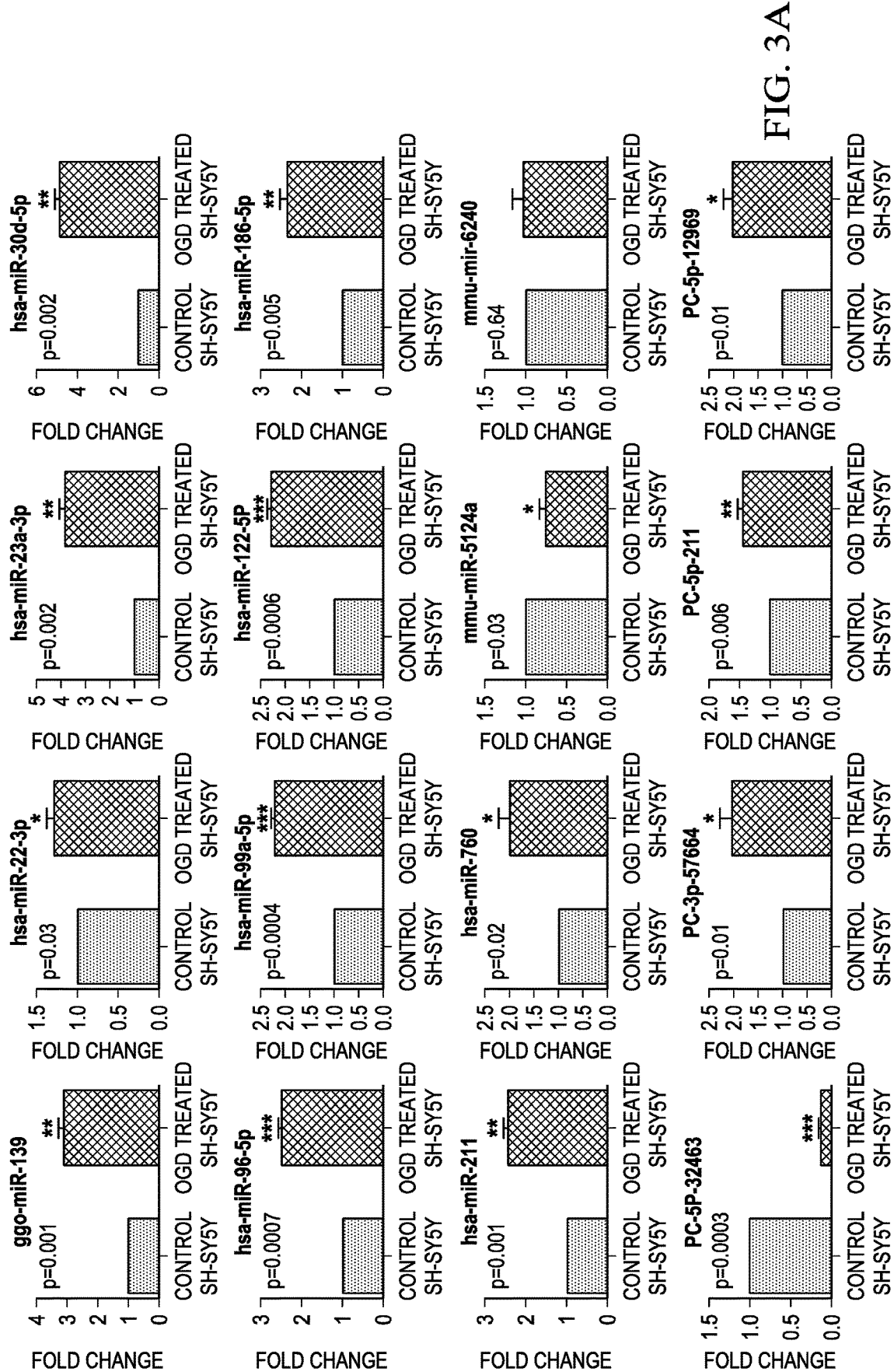
FIGS. 3A and 3B show.

Validation of serum miRNAs using lymphoblastoid IS cell lines. To further validate the miRNA sequencing data, expression of 16 miRNAs were measured in lymphoblastoid cell line strains (LCL) by real-time RT-PCR (data not shown). Seven miRNAs, mmu-mir-6240-p5 (P=0.007), ggo-miR-139 (P=0.002), hsa-mir-760 (P=0.001), PC-3p-57664 (P=0.0009), PC-5p-12969 (P=0.02), hsa-miR-122-5p (P=0.03) and hsa-miR-211-5p (P<0.0001) were upregulated in IS LCL compared with control LCL strains. PC-3p-32463 (P=0.01) and hsa-miR-30d-5p (P=0.01) were significantly down-regulated in the IS LCL strains (FIG. 2C). These results further confirmed the significant response of these four miRNAs; PC-3p-57664, PC-5p-12969, hsa-miR-122-5p, hsa-miR-211-5p in IS pathogenesis.

miRNAs expression in OGD treated cells Human neuroblastoma cells (SH-SY5Y). To determine the involvement of miRNA expression in hypoxic-ischemic induced neuronal death, OGD-stimulated human neuroblastoma cells was monitored. The inventors selected 16 miRNAs for analysis based on a number of factors including, their expression levels in IS serum, postmortem IS brains and IS LCL strains. PC-5p-211 (P=0.006), ggo-miR-139 (P=0.001), hsa-mir-760 (P=0.02), hsa-miR-96 (P=0.0007), hsa-miR-99a-5p (P=0.0004), PC-3p-57664 (P=0.01), PC-5p-12969 (P=0.01), hsa-miR-122-5p (P=0.0006), hsa-miR-211-5p (P=0.001) were increased significantly in human neuroblastoma cells following OGD/R exposure compared to control cells (FIG. 3A). Mmu-miR-5124a (P=0.03), PC-3p-32463 (P=0.0003) were significantly down-regulated in the OGD treated cells.

Figure 3B:
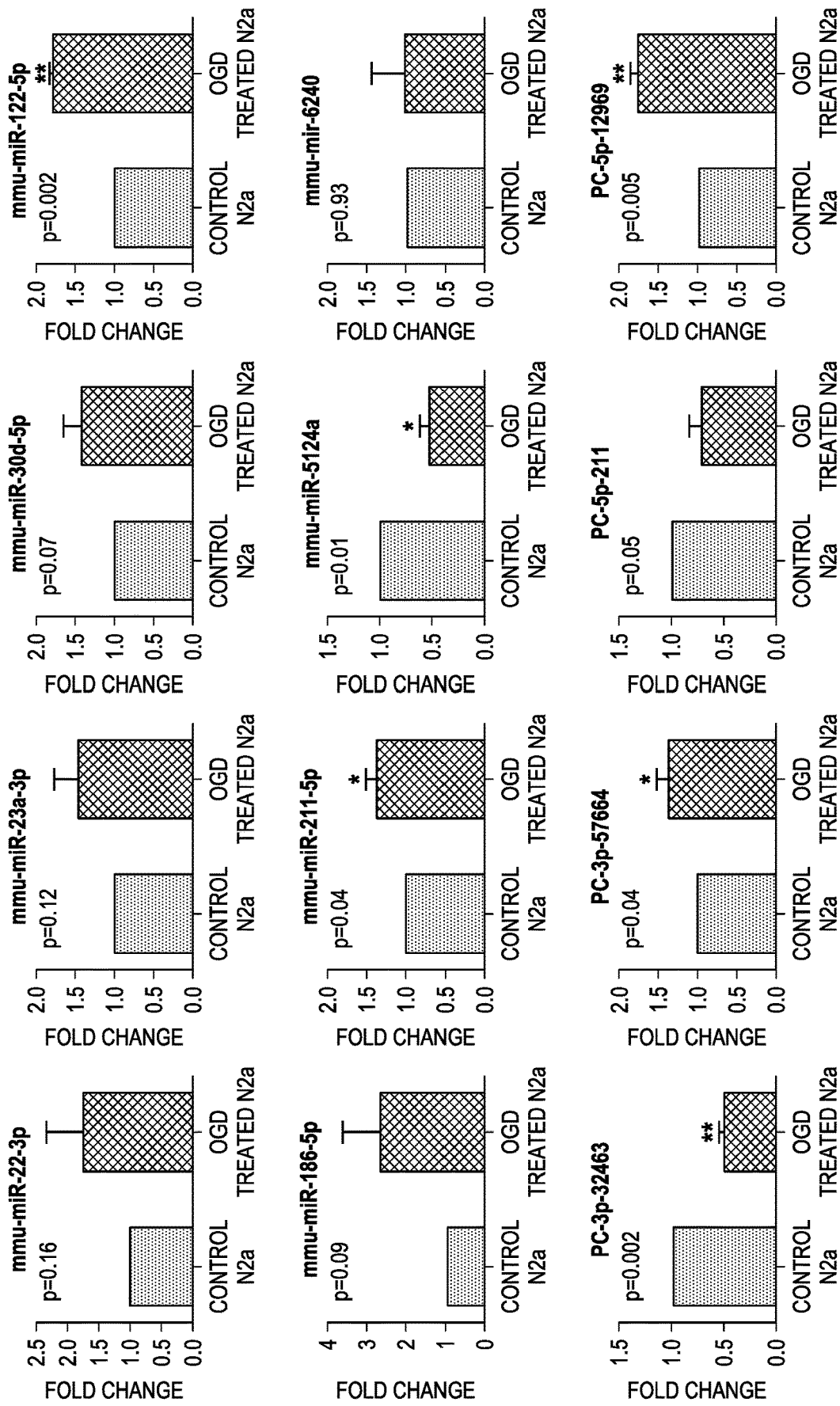

Mouse neuroblastoma (N2a) cells. The inventors further evaluated the miRNA expression profiles of the OGD/R-activated N2a cells. To test the hypothesis, the inventors selected 12 miRNAs. In these, 9 miRNAs that exhibited significantly altered expression levels between the hypoxic and normoxic conditions. PC-3p-57664 (P=0.04), PC-5p-12969 (P=0.005), mmu-miR-122-5p (P=0.002), mmu-miR-211-5p (P=0.04) were upregulated significantly in mouse neuroblastoma cells following OGD exposure compared to normoxia treated cells (FIG. 3B). Mmu-miR-5124a (P=0.01), PC-3p-32463 (P=0.002) were significantly down-regulated in the OGD treated cells.

Figure 4:
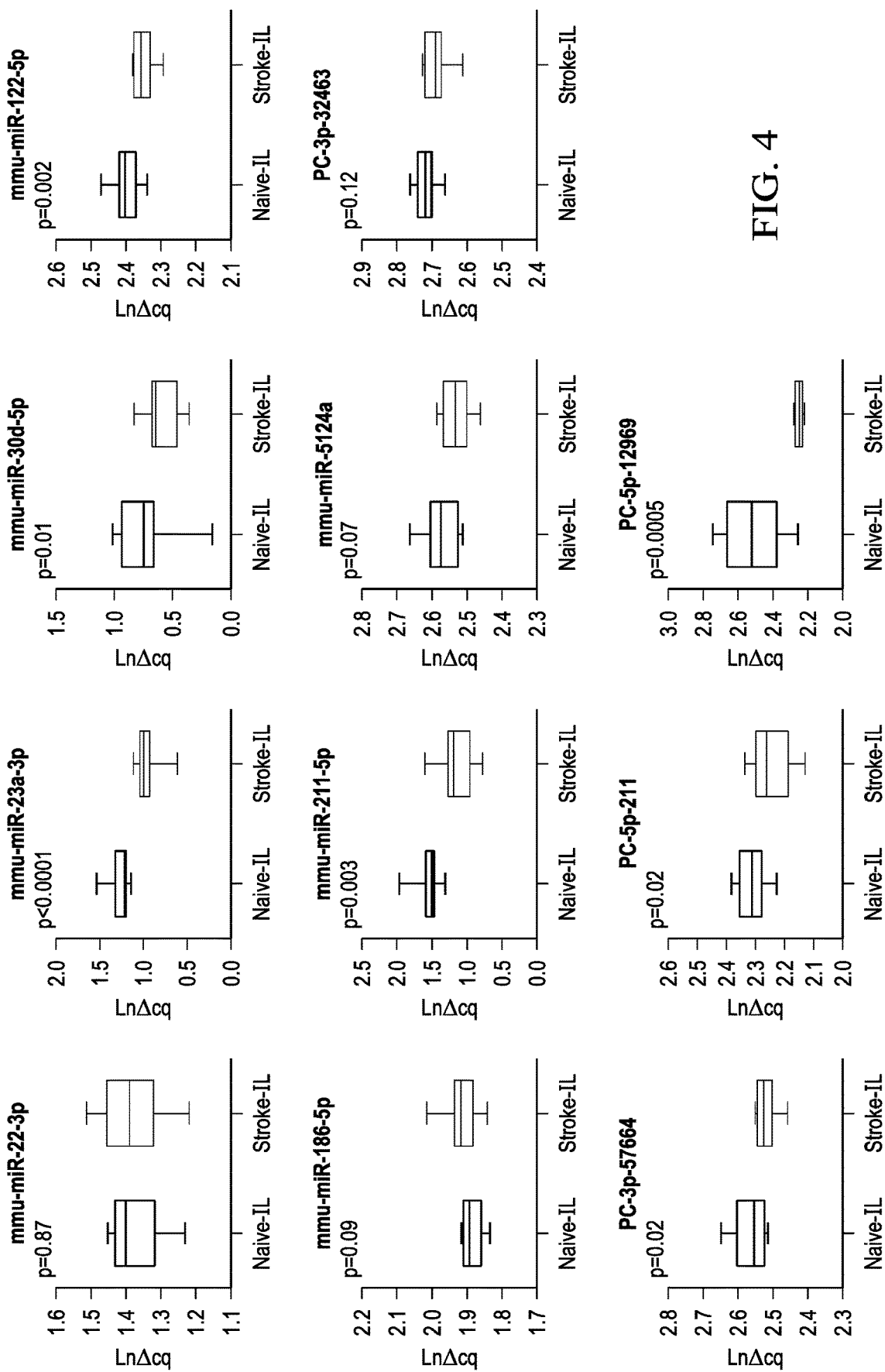
FIG. 4 shows quantitative RT-PCR analysis of miRNAs in hippocampus region of stroke hypoxia ischemia model. Fold change was calculated by $2^{-\Delta\Delta C_T}$ method. Significant difference among groups were calculated by paired t-test with two-tailed P<0.05 is considered significant.
Figure 5A:
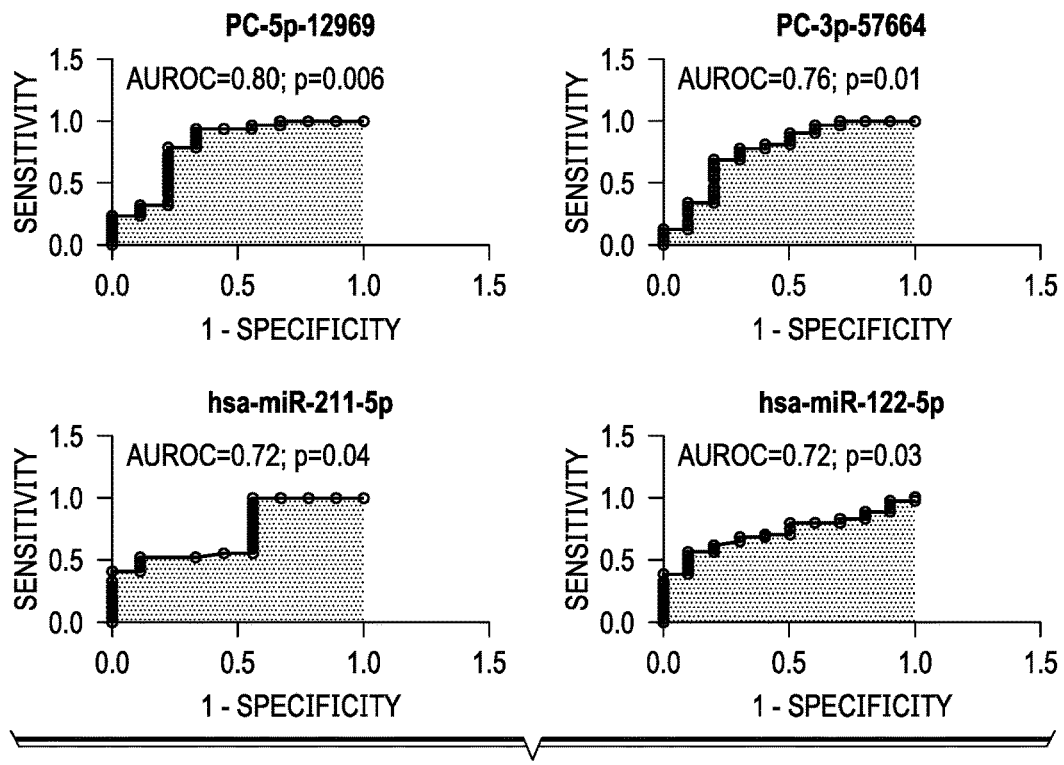
FIGS. 5A to 5D show receiver operating characteristics curve analysis of serum miRNAs as diagnostic biomarkers differentiating IS patients from healthy controls.
Figure 5B:
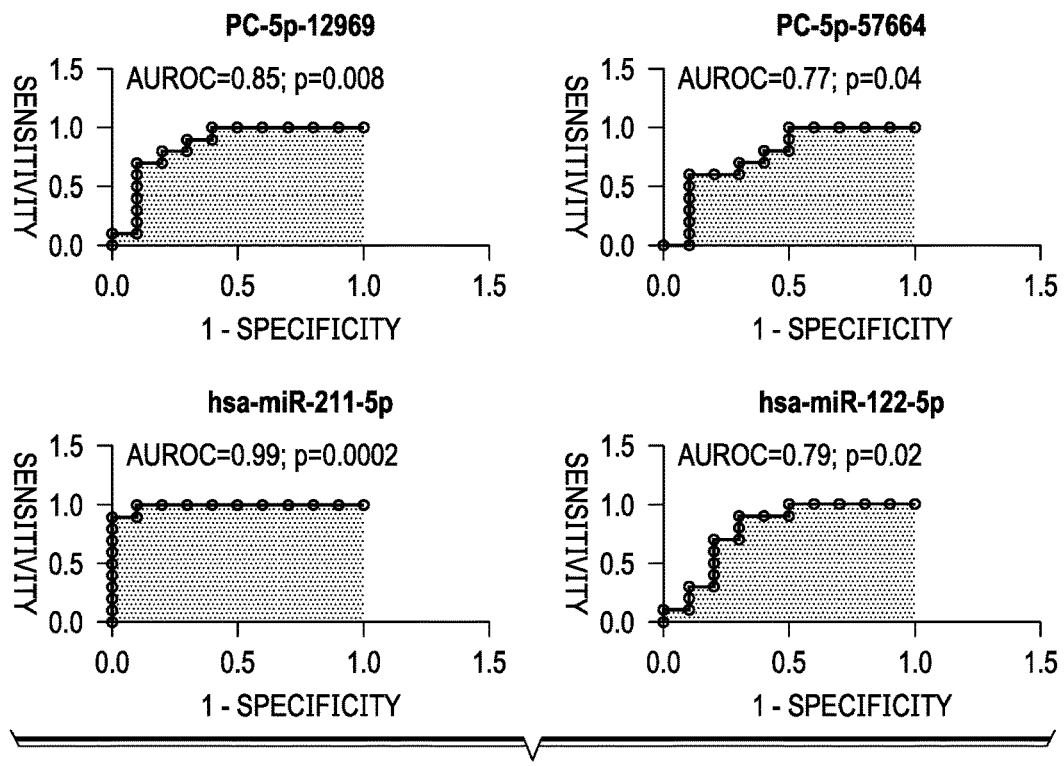
Figure 5C:
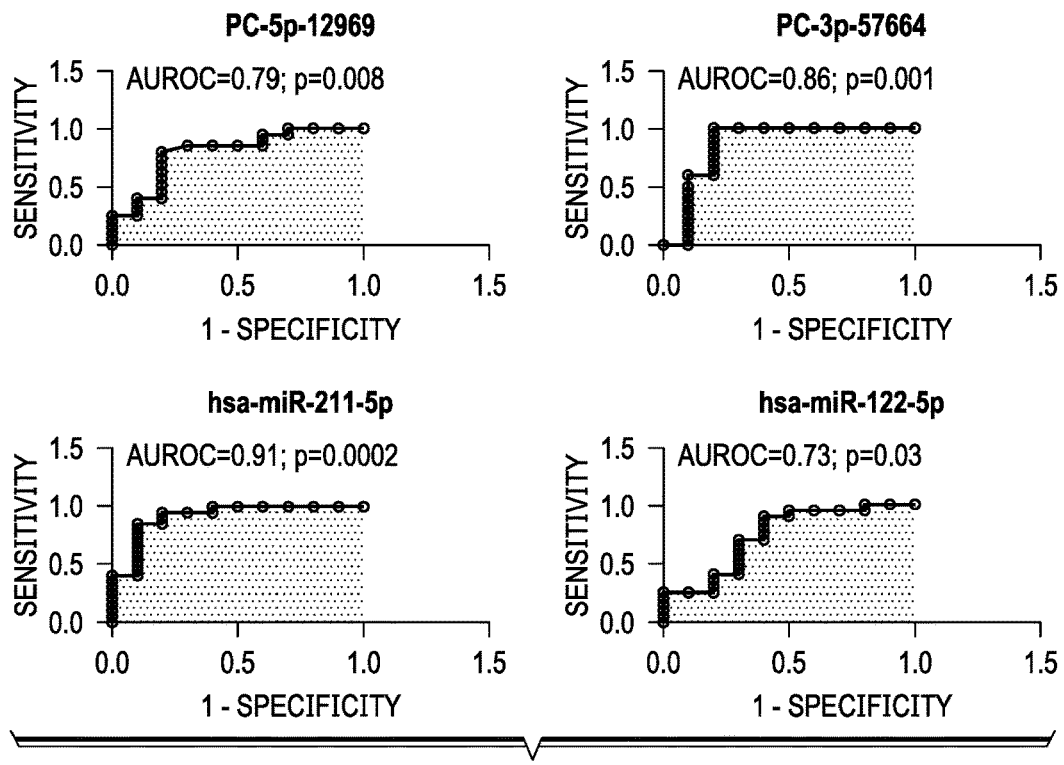
Figure 5D:
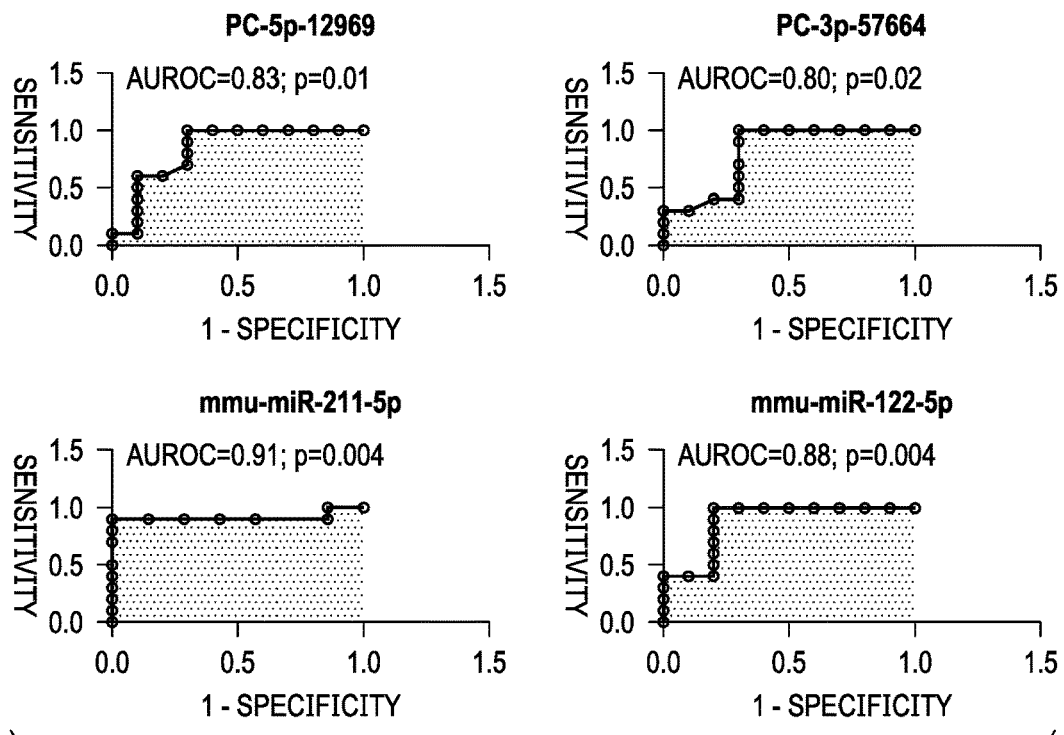

Differential expression of miRNAs in the brain of hypoxia and ischemia (HI) induced neonatal mice. To verify the accuracy of miRNA sequencing results, the inventors selected 11 miRNAs for further validation in brains of hypoxia and ischemia induced mouse models. The inventors studied 4 different brain regions, including hippocampus, striatum, cerebral cortex and cerebellum from HI induced neonatal and control, naïve mice. Out of 11 miRNAs, the following five miRNAs mmu-miR-211-5p (P=0.003), PC-5p-211 (P=0.02), PC-3p-57664 (P=0.02), PC-5p-12969 (P=0.0005), mmu-miR-122-5p (P=0.002) were significantly upregulated in the hippocampus of HI mice when compared with that of naïve control mice (FIG. 4).

Receiver operating characteristics (ROC) curve analysis. Expression of four miRNAs (PC-3p-57664, PC-5p-12969, hsa-miR-122-5p, hsa-miR-211-5p) consistently upregulated throughout the validation analysis. Therefore, the inventors evaluated the diagnostic value of these four miRNAs by plotting ROC curve in IS serum, postmortem IS brains, LCL strains and HI stroke mouse models. The curves were plotted based on the ΔCt value of candidate miRNAs expression in different sources. Upon analysis, PC-3p-57664 (AUROC=0.76; 95% CI: 0.571-0.953; P=0.01), PC-5p-12969 (AUROC=0.80; 95% CI: 0.6053-0.996; P=0.006), hsa-miR-122-5p (AUROC=0.72; 95% CI: 0.569-0.874; P=0.03), hsa-miR-211-5p (AUROC=0.72; 95% CI: 0.533-0.919; P=0.04) showed significant area under curve in IS serum samples compared with the healthy controls. The same trend was observed in postmortem IS brains, IS LCL strains as well in the HI stroke mice (FIGS. 5A-D). Thus, ROC analysis confirmed that the profile of the four serum miRNAs could be a simple, specific, and noninvasive molecular biomarker for diagnosing IS.

The present inventors identified early detectable peripheral biomarkers for IS in the residents of rural West Texas. MiRNAs have been identified as circulating biomarkers in several diseases, including IS (13-15). The inventors used illumina deep sequencing and further validation analysis revealed that 16 circulating miRNAs that distinguishes between IS patients and healthy controls. Of the 16 miRNAs differentially expressed between IS patients and healthy controls, 12 miRNAs are previously reported in stroke and other diseases and four miRNAs are novel and unreported miRNAs. As of yet, no study is reported to validate the expression of these miRNAs in postmortem IS brains, IS LCL strains, OGD/R treated human and mouse neuroblastoma cells and HI stroke mice. For the first time, the inventors identified the novel miRNAs (PC-3p-57664, PC-5p-12969) in IS serum samples from the residents of rural West Texas and verified their expression in mice as well. MiRNAs are cell specific, interestingly these novel candidates were consistently upregulated in all stroke sources and showed a strong correlation with stroke pathology. Hence, these miRNAs provide unique biomarkers for stroke.

Chen and Zhang (2010), identified the variant rs2507800 in the 3'-untranslated region of angiopoietin-1 that might reduce the risk of stroke by interfering with hsa-miR-211 binding site (16). Interestingly in these results, hsa-miR-211-5p was upregulated in IS patients. Hsa-miR-122 was identified to be related to human stroke based on the Human MicroRNA Disease Database (17). Another study investigated miRNA expression profile and found that miR-122 was down-regulated (18). Jickling et al. (2014) identified miR-122 were decreased in acute IS patients compared to controls (9). Hsa-miR-23a and hsa-miR-22 were significantly down-regulated in stroke patients (19). MiR-23a levels differed in male and female ischemic brains, providing evidence for sex-specific miRNA expression in stroke (20). Hypertension is a well-established risk factor for stroke. Several studies showed that miRNAs were known to impact the state of hypertension directly or indirectly. In another research, miR-30d was down-regulated known to be involved in hypertension (21). Interestingly, in this study it was also found that miR-30d was down-regulated, which clearly meant there was a link between stroke and hypertension. A study by Long et al. (2013) identified that circulating miR-30a was markedly down-regulated in all patients with IS until 24 weeks (22).

Postmortem human brain tissue was being used for quantifying cellular and molecular markers of neural courses with the area of improved understanding the variations in the brain caused by neurological diseases (23). However, the miRNA expression levels and molecular characterizations were not investigated using postmortem IS brains. This is the first study to validate the miRNAs using postmortem IS brain specimens. MiRNAs PC-3p-57664, PC-5p-12969, hsa-miR-122-5p and hsa-miR-211-5p were consistently upregulated and PC-3p-32463, PC-5p-211, ggo-miR-139, hsa-miR-30d-5p, mmu-mir-6240-p5, hsa-miR-23a-3p were significantly down-regulated in the IS brains.

A recent study reported that a decrease of brain miRNA-122 level was deleterious and could be considered as an early marker of stroke in the stroke-prone spontaneously hypertensive rat (24). Elevating miR-122 improves stroke outcomes and this occurred via down-regulating miR-122 target genes in blood leukocytes (25). Down-regulation of miRNA-30a improves ischemic injury through enhancing beclin 1-mediated autophagy in N2a cells and cultured cortical neurons after OGD, and mouse brain with MCAO-induced ischemic stroke (26).

Lymphoblastoid cell lines are the biological resources that have been used in various research fields related to human genetics, pharmacogenomics and immunology (27, 28). LCLs have the potential to disclose at least a subset of brain-related miRNAs implicated in stroke. Hypoxia induces time-dependent alteration of the expression levels of miRNAs suggesting their involvement in the cellular response to ischemic injury (29). In the present study, the inventors performed miRNA expression in IS LCL strains and OGD/R on human and mouse neuroblastoma cells to mimic ischemia in vitro. This is the first study to examine the roles of miRNA expression variations in IS LCLs.

MiRNAs have essential roles in brain function, including neurogenesis, neural development, and cellular responses leading to changes in synaptic plasticity. They are also implicated in neurodegeneration and neurological disorders, in responses to hypoxia and ischemia, and in ischemic tolerance induced by ischemic preconditioning (30). Expression levels of few miRNAs could be differently modulated in both in vivo and in vitro experimental models (25, 31). The inventors assessed the expressions of 11 miRNAs using a Hypoxia and ischemia induced in postnatal day nine (P9) C57BL/6J mice. Hippocampal region of the HI induced neonatal mouse brain showed the most consistent differential expression of miRNA compared to other regions. A recent global expression of miRNAs in a P10 rat model of cerebral HI, found that miR-30d-5p was one of the most deregulated miRNAs in neonatal brains in response to HI. Collectively, these results indicated that miR-30d-5p modulated survival programs of neural cell by regulating autophagy and apoptosis (32).

The miRNAs identified in the present study have implications for both consequences and risk factors of stroke. In the current study, the inventors investigated serum samples from ischemic stroke patients and identified that differentially expressed miRNAs are the consequence of disease process, and that these differentially miRNAs can be used to target novel therapeutic targets for ischemic stroke, as described herein.

In summary, miRNA sequencing analysis of IS serum samples showed significant deregulation of sixteen miRNAs. Among 16 miRNAs, four miRNAs: PC-3p-57664, PC-5p-12969, hsa/mmu-miR-122-5p, hsa/mmu-miR-211-5p were almost consistently unregulated in human IS serum samples, human postmortem IS brain specimens, human lymphoblastoid IS cell lines, OGD/R treated human and mouse neuroblastoma cells and HI stroke mouse models. ROC curve analysis in serum and postmortem brain also confirmed their diagnostic potential for stroke. Further, GO and KEGG pathway analysis showed the regulation of many stroke related genes and pathways by these miRNAs. Based on intense analysis, the inventors conclude that circulatory levels of PC-3p-57664, PC-5p-12969, miR-122-5p, miR-211-5p are biomarkers for the diagnosis of IS.

Enrollment of study samples. For the present study, 34 IS patients (13 males, 21 females: mean age of 62.88±11.94 years) and 11 healthy controls (5 males, 6 females: mean age: 62.63±6.6 years) were used as the study group. Sera samples were collected from patients and healthy controls under Facing Rural Obstacles to healthcare Now Through Intervention, Education & Research (FRONTIER) project based at Garrison Institute on Aging (GIA), Texas Tech University Health Sciences Center. The Institutional Review Board (IRB) protocol was approved for Project FRONTIER (IRB #L06-028). All the bio-specimens were stored at the GIA. Information on demographic characteristics, medical history, biochemical profile and established risk factors were recorded by using a standardized questionnaire (Supplementary Material, Table S5).

RNA extraction, Small RNA Library Construction. RNA was isolated from 1.5 mL of serum using Plasma/Serum RNA purification Midi Kit as per manufacturer's instructions (Cat No: 56100; Norgen Biotek Corp., Thorold, ON, Canada). All RNA samples were processed and analyzed by LC Sciences (Houston, Tex., USA). The quality and quantity of the RNA samples were tested using an Agilent 2100 Bioanalyzer (Agilent). A small RNA library was generated using the Illumina Truseq™ Small RNA Preparation kit according to Illumina's TruSeq™ Small RNA Sample Preparation Guide [(15004197 C), Illumina Inc., Part #1004239 Rev. A, 2008; Catalog #RS-930-1012, Part #15004197 Rev. B, January 2011].

Primary screening by deep sequencing and data analysis. The purified cDNA library was used for cluster generation on Illumina's Cluster Station and then sequenced on Illumina GAIIx following vendor's instruction for running the instrument. Raw sequencing reads (40 nts) were obtained using Illumina's Sequencing Control Studio software version 2.8 (SCS v2.8) following real-time sequencing image analysis and base-calling by Illumina's Real-Time Analysis version 1.8.70 (RTA v1.8.70). The extracted sequencing reads were stored and then a proprietary pipeline script, ACGT101-miR v4.2 (LC Sciences), was used for sequencing data analysis. After the raw sequence reads, or sequenced sequences (sequ seqs) were extracted from image data, a series of digital filters (LC Sciences) were employed to remove various un-mappable sequencing reads. Impurity sequences due to sample preparation, sequencing chemistry and processes, and the optical digital resolution of the sequencer detector were also removed. Remaining sequ seqs with lengths between 15 and 32 bases were grouped by families (unique seqs), and were used to map with the reference database files.

Various "mappings" were performed on unique seqs against pre-miRNA (mir) and mature miRNA (miR) sequences listed in the latest release of miRbase (v21.0; ftp://mirbase.org/pub/mirbase/CURRENT/; Specific species: hsa; Selected species: ggo, ppa, ptr, ppy, ssy, age, 11a, sla, pbi, mml, mne, lca, cgr, mmu, rno, cfa, ocu, efu, aja, eca, mdo, sha, meu, oan, bta, chi, oar, tch, ssc) (33-35) or genome based on the public releases of appropriate species (V37.1; ftp.ncbi.nih.gov/genomes/Hsapiens). Mappings were also done on mirs of interest against genome sequence. Mappable unique seqs were mapped to other defined databases, such as mRNA, RFam, and Repbase (V37.1; ftp.ncbi.nih.gov/genomes/Hsapiens/RNA). Methods and criteria used for various mappings were documented in the ACGT-101 User's Manual. Sequences were mapped against reported miRNA, species' genomes, and other RNA databases (e.g., RFam, repase, mRNA) and were classified as follows:

I) Mappable reads mapped to selected mirs in miRbase
  1) Mirs mapped to species specific genome (*Homo sapiens*)
    i) Mirs are of specific species (*Homo sapiens*) (group 1a)
    ii) Mirs are of selected species (Mammalia) (group 1b)
    iii) Reads mapped to other locations too & Reads mapped only to the same
      locations in the genome as that of mirs (group 1c)
  2) Mirs un-mapped to species specific genome
    a) Reads mapped/un-mapped to species specific genome
      i) Extended sequences potentially form hairpins (group 2a)
      ii) Extended sequences potentially cannot form hairpins (group 2b)
      iii) Reads mapped to miRs of selected species (group 3a)
      iv) Reads unmapped to miRs of selected species (group 3b)

II) Mappable reads un-mapped to selected mirs in miRbase
  1) Reads un-mapped to mRNA, Rfam, and repbase
    a) Reads mapped to species specific genome
      i) Extended sequences potentially form hairpins (group 4a)
      ii) Extended sequences potentially cannot form hairpins (group 4b)
    b) Reads un-mapped to species specific genome (no hit)
    c) Reads mapped to mRNA, Rfam, or repbase (others)

Validation of differently expressed serum miRNAs using quantitative real-time RT-PCR. To support the data obtained from the deep sequencing results, qRT-PCR analysis was performed to validate further. One µG of total RNA was reverse transcribed using miRNA First-Strand cDNA synthesis kit (Agilent Technologies Inc., CA, USA), following manufacturer's instructions. Resulting cDNAs were diluted with 20 µL of RNase-free water and stored at −80° C. for further analysis (36). Primers for 16 miRNAs were synthesized commercially (Integrated DNA Technologies, Inc. Iowa USA) (Supplementary Material, Table S2). U6, one of the uniformly expressed small RNAs, was used as the internal control for real-time RT-PCR. Briefly, 1 µL of miRNA-specific forward primer (10 µM), 1 µL of a universal reverse primer (3.125 µM) (Agilent Technologies Inc., CA, USA), 10 µL of 2×SYBR® Green PCR master mix (Applied Biosystems, NY, USA), and 1 µL of cDNA were mixed. To this mixture RNase-free water was added up to a 20 µL of final volume. The reactions were amplified for 5 min at 95° C., followed by 40 cycles of 95° C. for 10 sec, 60° C. for 15 sec and 72° C. for 25 sec at 7900HT Fast Real Time PCR System (Applied Biosystems, USA). All reactions were performed in triplicate, and the controls (no template and no RT) were included for each gene, and the data were expressed as the mean±SD. Fold change of each miRNAs were calculated as described previously (37). The threshold cycle (CT) values were automatically determined by the instrument, and the fold change of each miRNAs were calculated using the following equation: the formula ($2^{-\Delta\Delta ct}$), where $\Delta$Ct was calculated by subtracting Ct of U6snRNA from the Ct of particular miRNAs target, and $\Delta\Delta$Ct value was obtained by subtracting $\Delta$Ct of particular miRNAs target in the controls from the $\Delta$Ct of miRNAs target in the IS.

Postmortem brains from stroke patients and controls. In the present study, 20 post-mortem brain samples were investigated which consisted of 10 IS [5 males and 5 females: Age ranged from 57-91 years (78.3±11.89) and post-mortem interval (PMI) varied from 4-23.9 hours (average 16.48 hours)] and 10 normal control subjects [5 males and 5 females: Age ranged from 67-91 years (76.9±8.62) and post-mortem interval (PMI) varied from 11.8-25 hours (average 17.99 hours)] were obtained from the Human Brain and Spinal Fluid Resource Center (Los Angeles, Calif.) and Harvard Brain Tissue Resource Center (HBTRC) through NIH NeuroBiobank. These brain banks were responsible for obtaining subject consent and the unidentifiable coding of subject information. The study protocol was approved by the Institute Ethical Committee at TTUHSC (IBC protocol number: 14013).

Lymphoblastoid Cell lines. Epstein-Barr Virus (EBV) transformed Lymphoblastoid cell lines (LCLs) from 20 IS patients (10 males, 10 females: mean age of 66.9±6.13 years) and 10 unrelated healthy subjects (5 males, 5 females: mean age of 62.8±4.91 years) were obtained from the Coriell Cell Repository. These samples had been collected and anonymized by National Institute of Neurological Disorders and Stroke (NINDS), and all subjects had provided written consent for their experimental use. LCLs were cultured in Roswell Park Memorial Institute Medium 1640 (RPMI 1640 medium) with 2 mM L-glutamine (Gibco, Carlsbad, Calif., #11875) supplemented with 15% heat-inactivated FBS.

Induction of neonatal hypoxia and Ischemia. Hypoxia and ischemia (HI) was induced in postnatal day nine (P9) C57BL/6J mice. The pups were anesthetized with isoflurane (Butler Schein Animal Health Supply, Reno, Nev.) (5% for induction, 2-3% for maintenance) in 30% oxygen mixed with nitrous oxide. The body temperature of the pups were maintained at 36° C. using a heated surgical table (Molecular Imaging Products, Bend, Oreg.). Under a surgical microscope (Nikon SMZ-800 Zoom Stereo, Nikon, Melville, N.Y.), a midline skin incision was made and the trachea was visualized through the muscle overlying it. The left common carotid artery was freed from the left common jugular vein and left vagus nerve by blunt dissection, electrically cauterized and cut. The incision was injected with 0.5% bupivacaine and closed with a single 6.0 silk suture. Animals were returned to their dams and monitored continuously for a 2 h recovery period. To induce unilateral ischemic injury, the animals were placed in a hypoxia chamber (BioSpherix Ltd, Redfield, N.Y.) equilibrated with 10% $O_2$ and 90% $N_2$ at 36° C. for 50 min. This is a well-characterized model of neonatal HI and results in reproducible brain injury ipsilateral (IL) to the electrocauterized left common carotid artery (38-41). Naïve mice were not exposed to HI or any surgical intervention. Mice were decapitated for collection of fresh tissue of the regions of striatum, hippocampus, cortex, and cerebellum on day 3 (P12) post-HI (42). After extraction, the fresh tissues were kept in −20° C. for 1 day and in −80° C. for long term storage. All procedures on animals were carried out in adherence with NIH Guide for the Care and use of Laboratory Animals and approved by the Institutional Animal Care and Use Committee at the University of Wisconsin-Madison.

Cell Cultures. The human neuroblastoma cell line SH-SY-5Y and mouse neuroblastoma cell line N2a were grown in Dulbecco's modified Eagle's medium/F12 (1/1) (DMEM/F12, Gibco Life Technologies, Carlsbad, Calif., #11320), minimum essential media respectively containing 10% fetal bovine serum (FBS), penicillin (100 U/mL), streptomycin (100 μG/mL). The cultures were maintained at 37° C. in 95% air, 5% $CO_2$ in a humidified incubator. After the cells were seeded, they were allowed to grow for 24-48h or until 80% confluence in 6-well plates then they were used for experimentation.

Oxygen and Glucose Deprivation/Reoxygenation Protocol. Oxygen and glucose deprivation/reoxygenation (OGD/R) is a well-established in vitro model to study the pathology and pharmacology of ischemic damage, OGD/R was achieved using methods published earlier (43-46). Culture media were replaced with deoxygenated, no glucose DMEM (Gibco, Carlsbad, Calif., #11966) and placed in hypoxia chamber (Biospherix, ProOx model 110) with 95% $N_2$ and 5% $CO_2$ for 4 hours at 37° C. to represent OGD condition. After the appropriate time, the culture plates were removed from the hypoxia chamber. Prior to re-oxygenation, cells were washed in PBS and the medium was replaced with complete culture medium then placed in a humidified incubator at 37° C. for 20-24 hours to represent reoxygenation.

MiRNAs extraction from tissues and cell pellets and qRT-PCR. Total RNA was isolated from the 80 mg of tissues and cell pellets using the TriZol RT reagent (Ambion, USA) as per manufacturer instructions. MiRNAs extraction and cDNA synthesis were followed as described earlier (36). The quality and quantity of the RNA were analyzed by Nano-Drop analysis. The value of absorbance of each RNA sample ($A_{260}/A_{280}$) was 1.8 to 2.0. cDNA was synthesized from 1 μG of RNA using miRNA First-Strand cDNA synthesis kit (Agilent Technologies Inc.).

Target gene prediction and enrichment analysis. MiRNAs of interest were selected based on the statistical significance, fold change difference and biological rationales. Target gene prediction was performed by using TargetScan 6.0 (www.targetscan.org). For human, the program searches were run to match the miRNA seed regions and orthologous at 3' UTRs of human genes (47). Gene function enrichment and biological pathway analysis were performed using DAVID online tool suite (david.ncifcrf.gov) (48). Validated and predicted target genes were uploaded at Gene List Manager according the tool instructions. Gene function enrichment and pathway analysis results were obtained and given in supplementary material Figures S5A, S5B and S5C.

Statistical analysis. Data were presented as means±SD for other variables. The qRT-PCR validation analysis was based on the $2^{-\Delta\Delta CT}$ value of genes in each sample from IS and healthy controls. The Cq values of miRNAs were displayed as LnΔCq for statistical analysis (49). P-value was calculated, based on the paired and unpaired t-tests for analyzing two groups. MiRNAs levels between the probable IS and healthy controls were analyzed using a two-sided nonparametric Mann-Whitney test. Sensitivity and specificity of measured variable for IS biomarker were examined using a receiver operating characteristic (ROC) curve analysis under a nonparametric approach. P value<0.05 was considered to be statistically significant. All analyses were performed by GraphPad Prism (version 6.0; GraphPad Software, La Zolla, Calif.).

Example 2. Effects of microRNA 'PC-5P-12969' in Ischemic Stroke Patients

To determine the protective and/or adverse effects of microRNA 'PC-5P-12969' in ischemic stroke patients, the inventors performed cell culture experiments using 1) normal condition and 2) oxygen glucose deprivation similar to ischemic stroke condition. The inventors assessed cell viability and apoptosis assays using overexpression (agomirs) and knockdown (antagomirs) of microRNA PC-5P-12969 in human neuroblastoma (SHSY-5Y) cells.

Using bioinformatics tools, the inventors also assessed binding site analysis of microRNA PC-5P-12969—in other words, the inventors assessed interacting mRNA transcripts to PC-5P-12969 in the entire human genome.

Figure 6:
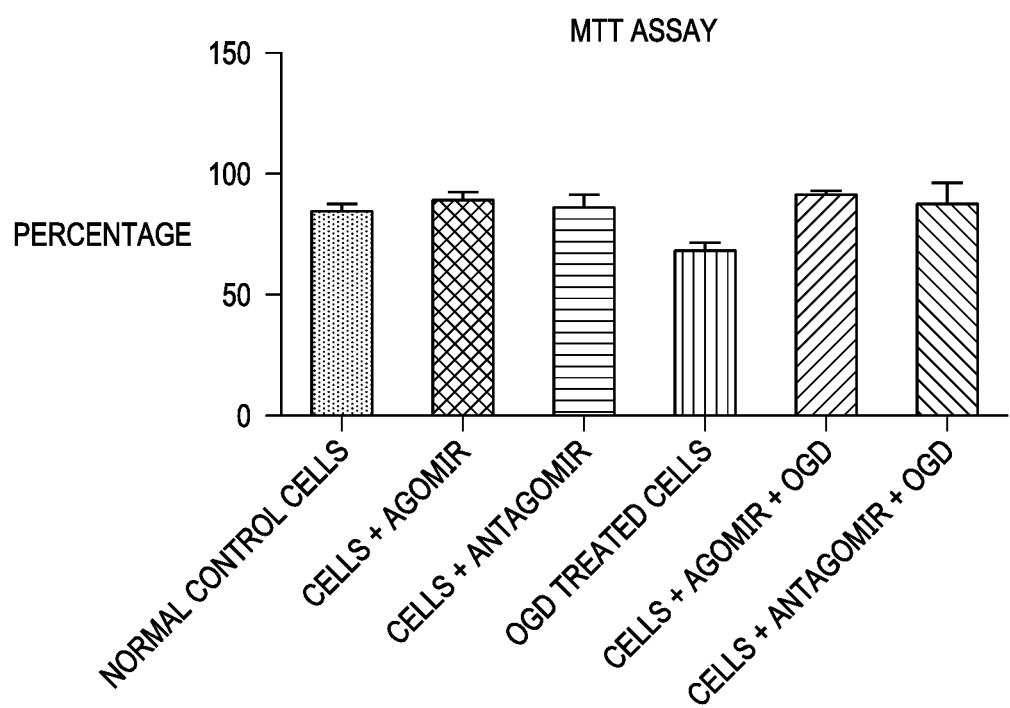
FIG. 6 is a graph that shows the effect on cells overexpressed with microRNA PC-5P-12969 exhibited increased cell survival and reduced apoptotic cell death relative to untreated cells, indicating that microRNA PC-5P-12969 is protective in normal condition, as measured with a 3-(4,5-dimethylthiazol-2-yl)-2,5-diphenyltetrazolium bromide (MTT) assay.
Figure 7A:
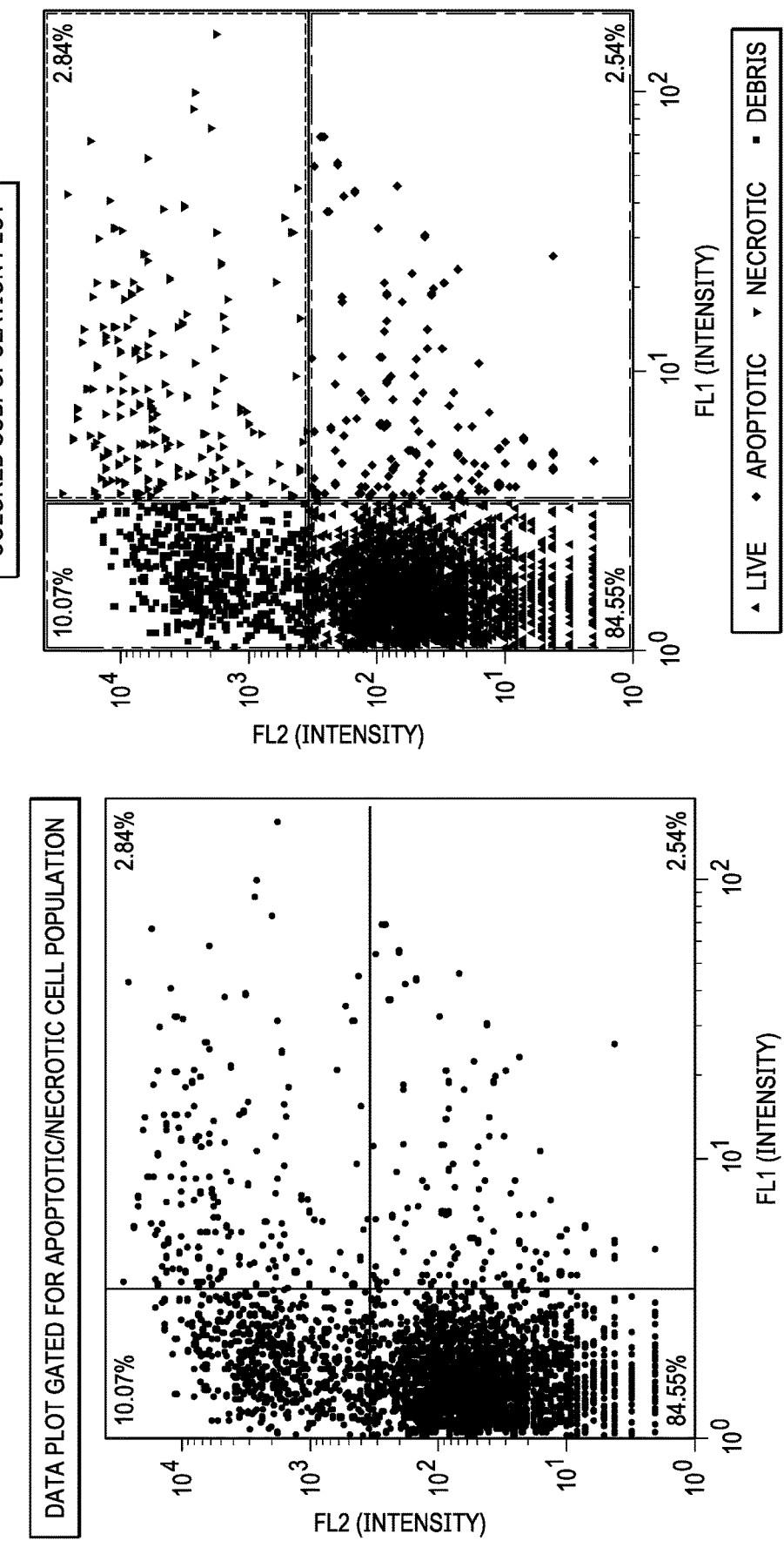
FIGS. 7A to 7F are graphs that show cells overexpressed with PC-5P-12969 microRNA and treated with oxygen glucose deprivation (similar to ischemic stroke) showed significantly increased cell survival and significantly reduced apoptotic cell death relative to oxygen glucose deprivation treated cells.
Figure 7B:
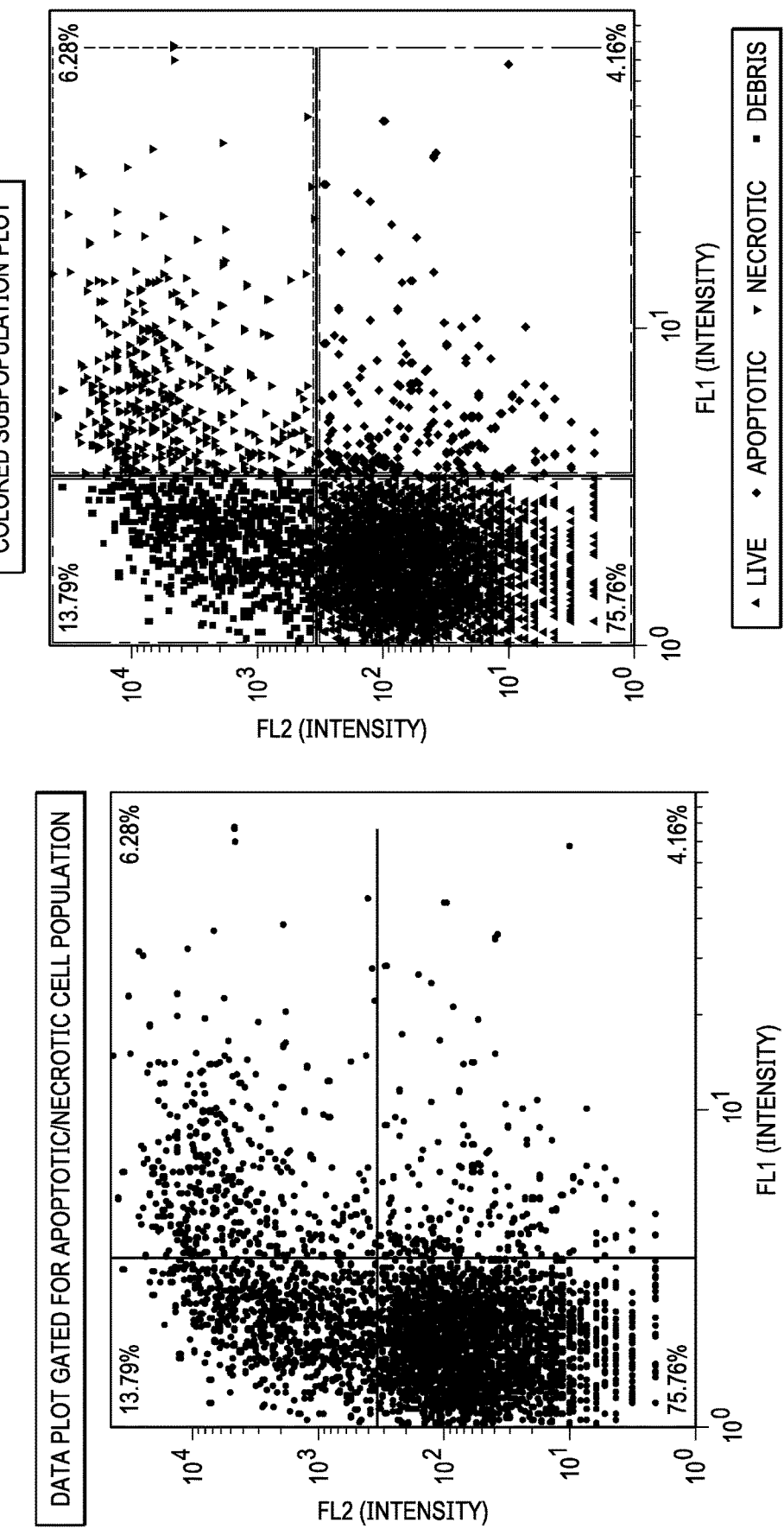
Figure 7C:
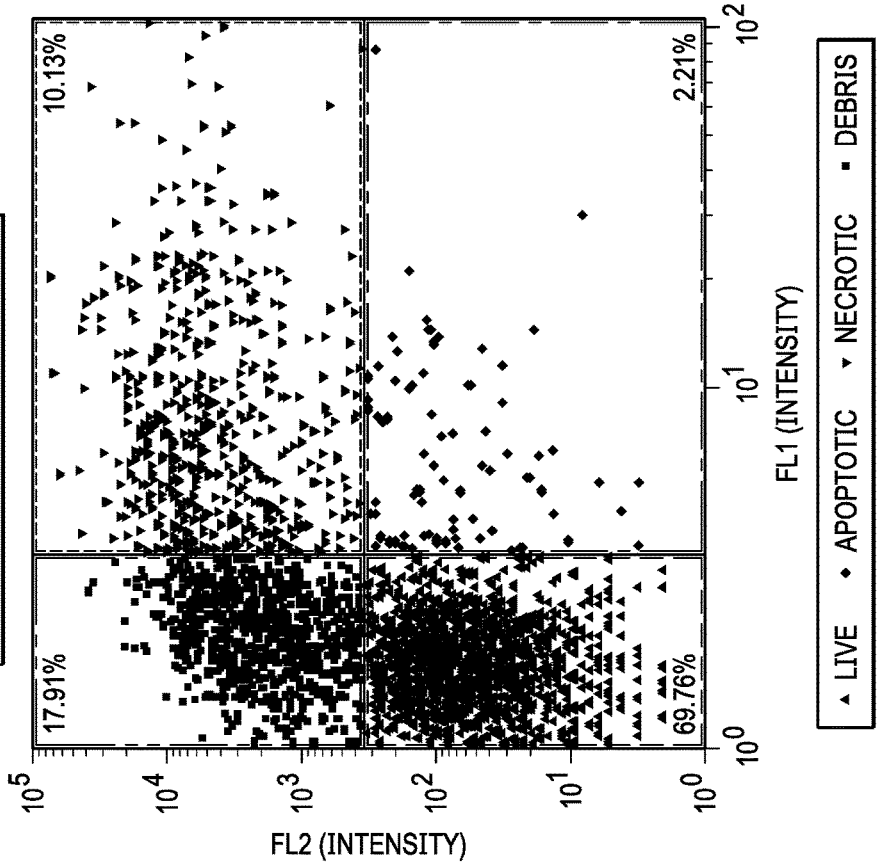
Figure 7C:
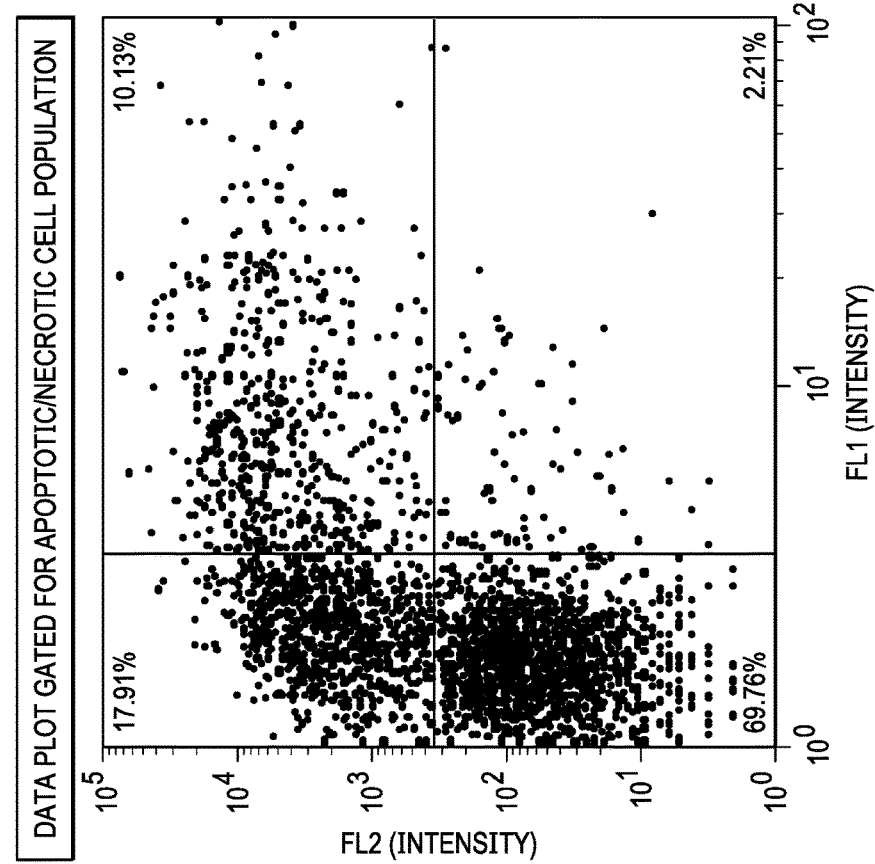
Figure 7D:
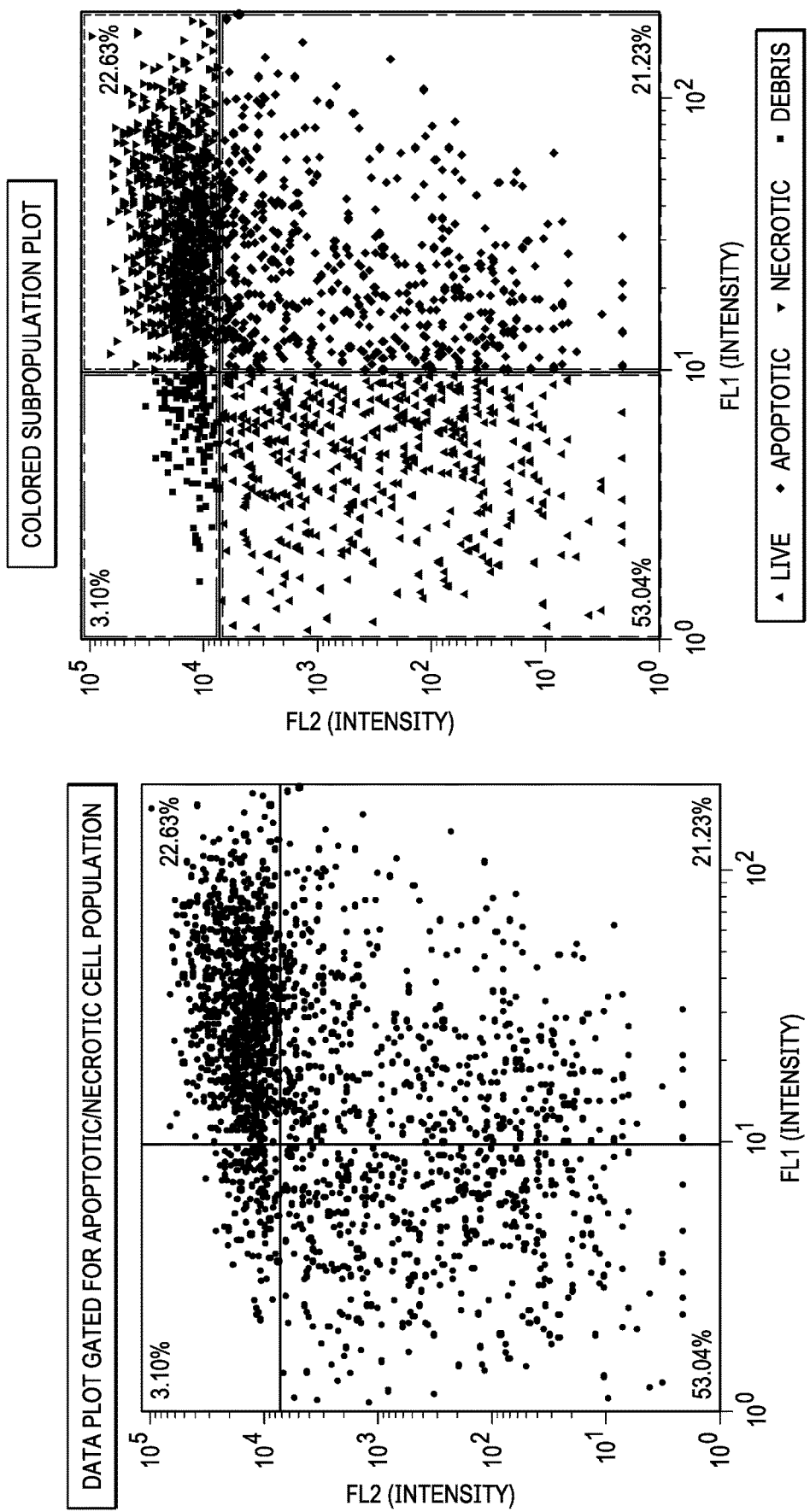
Figure 7E:
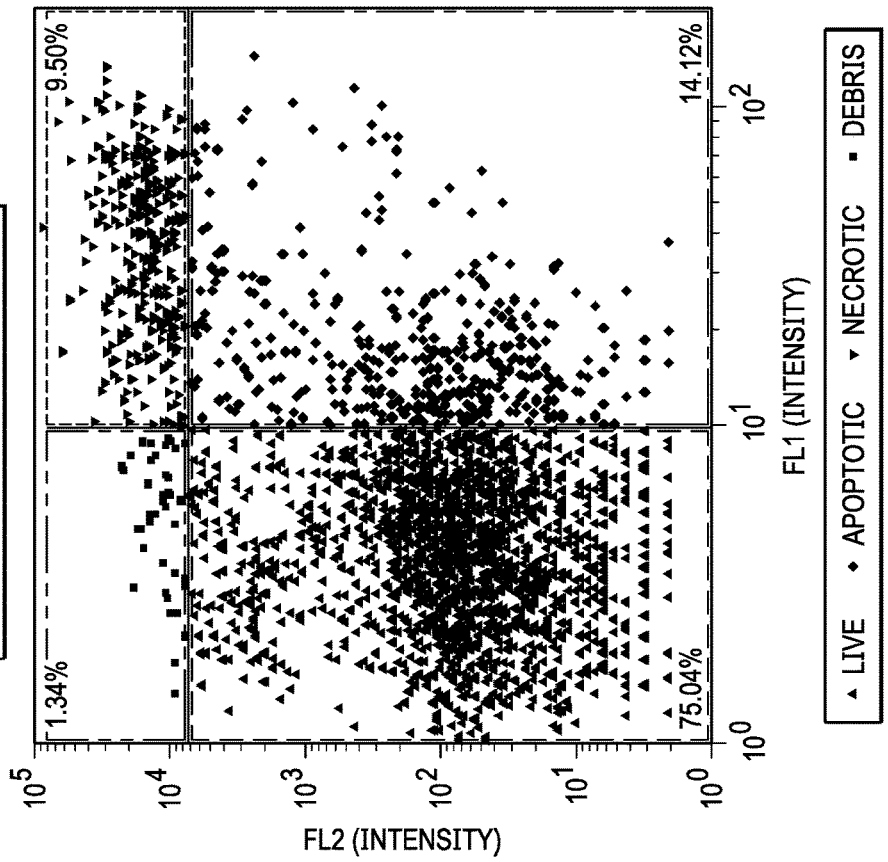
Figure 7E:
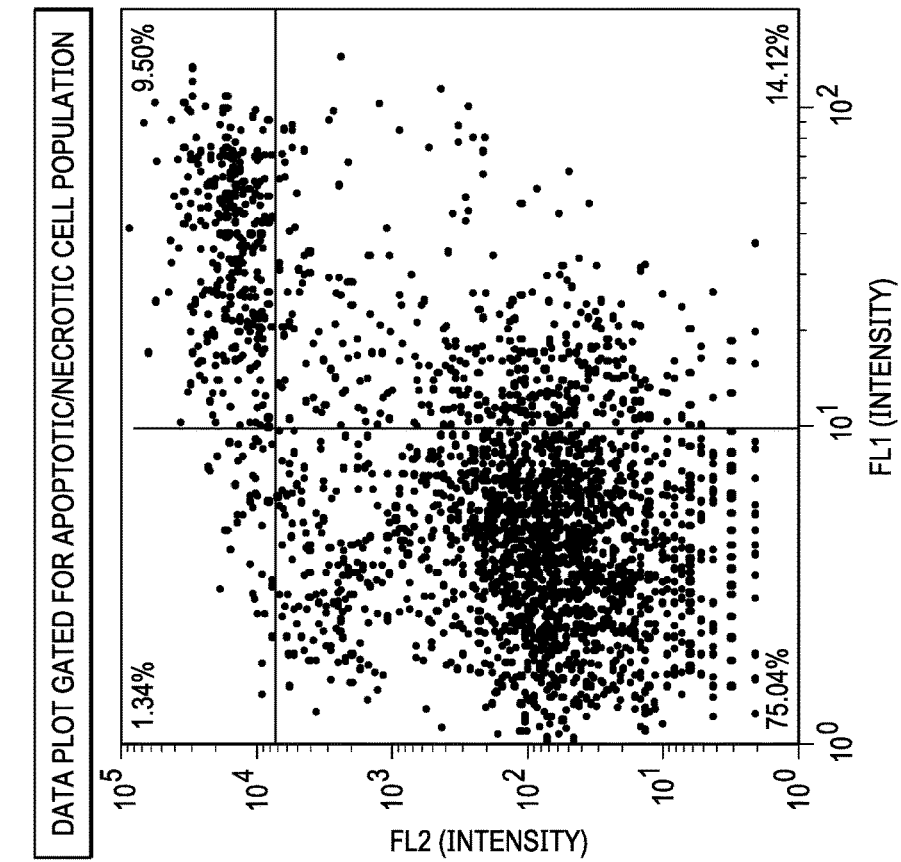
Figure 7F:
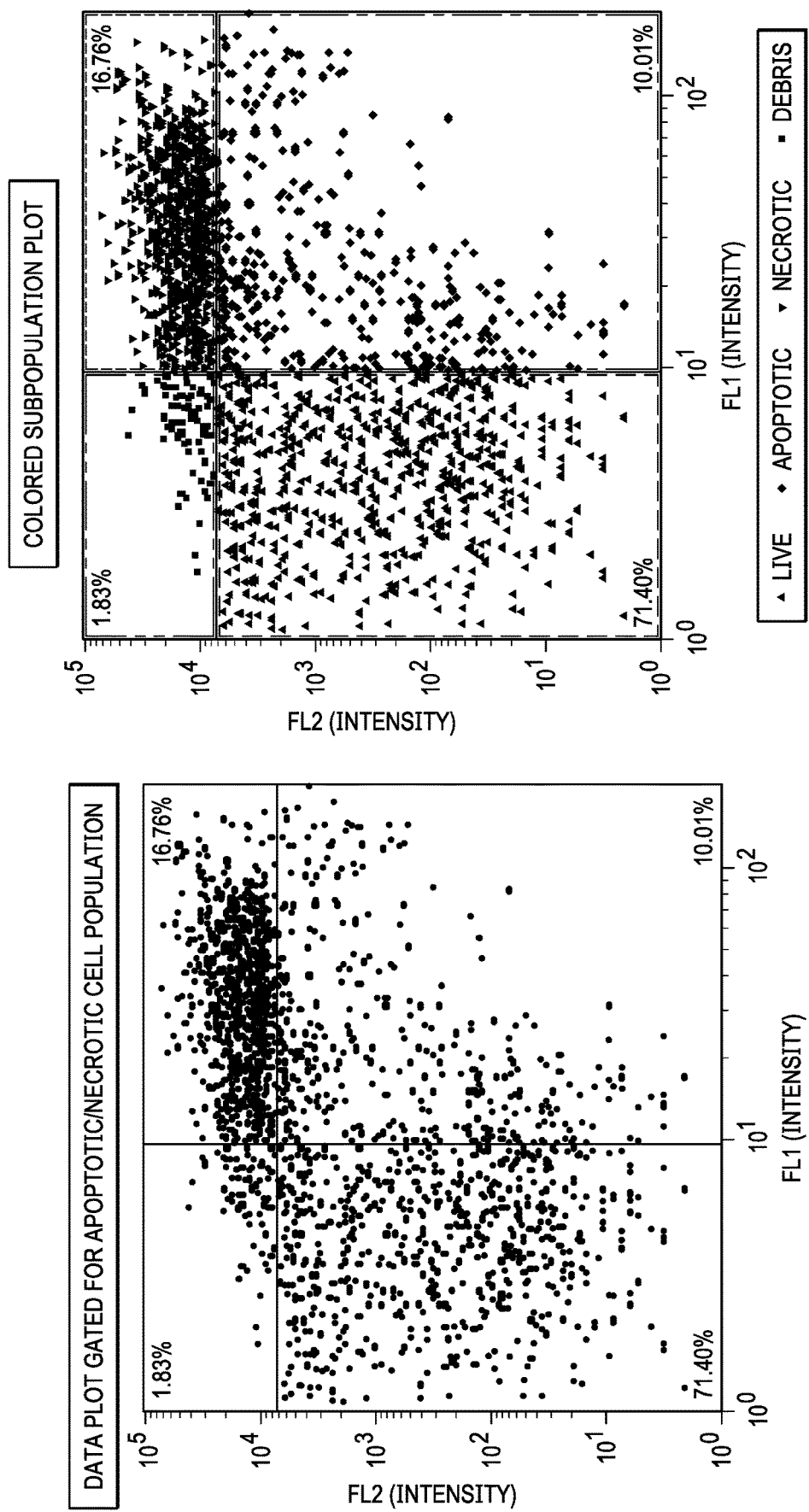

Cells overexpressed with microRNA PC-5P-12969 exhibited increased cell survival and reduced apoptotic cell death relative to untreated cells, indicating that microRNA PC-5P-12969 is protective in normal condition (FIG. 6). On the other hand, cells overexpressed with PC-5P-12969 microRNA and treated with oxygen glucose deprivation (similar to ischemic stroke) showed significantly increased cell survival and significantly reduced apoptotic cell death relative to oxygen glucose deprivation treated cells (FIGS. 7A-F).

Figure 8A:
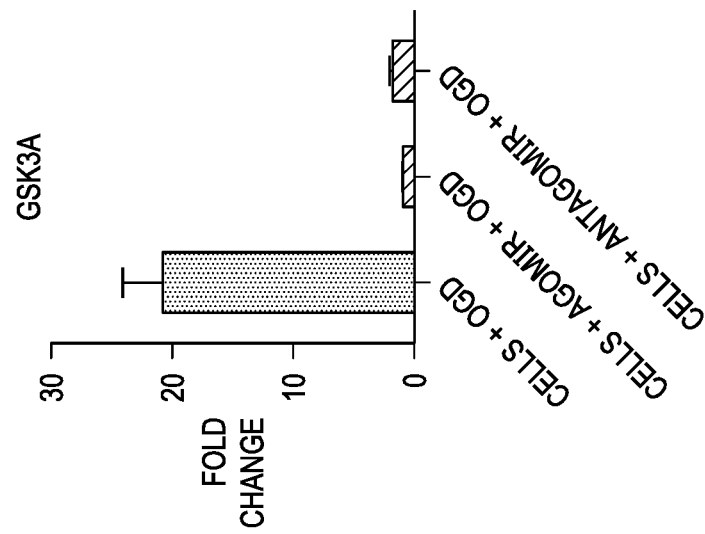
FIGS. 8A to 8C are graphs that show the levels of expression of, FIG. 8A GSK3A, FIG. 8B PARK2, and FIG. 8C HTRA2.
Figure 8B:
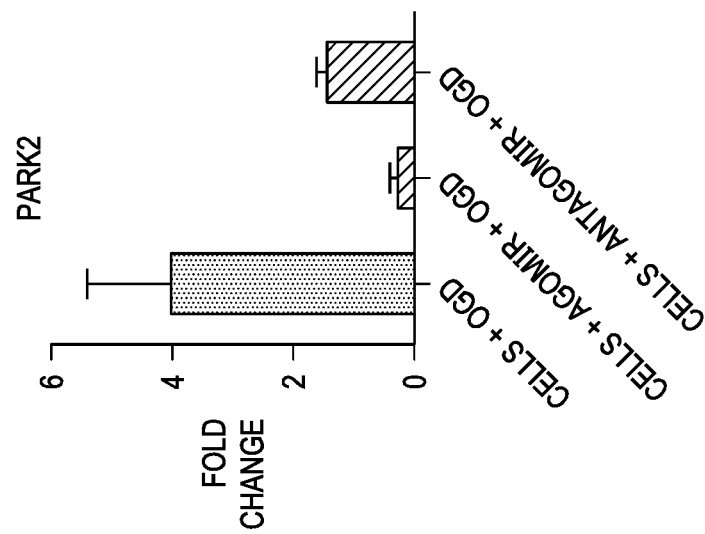
Figure 8C:
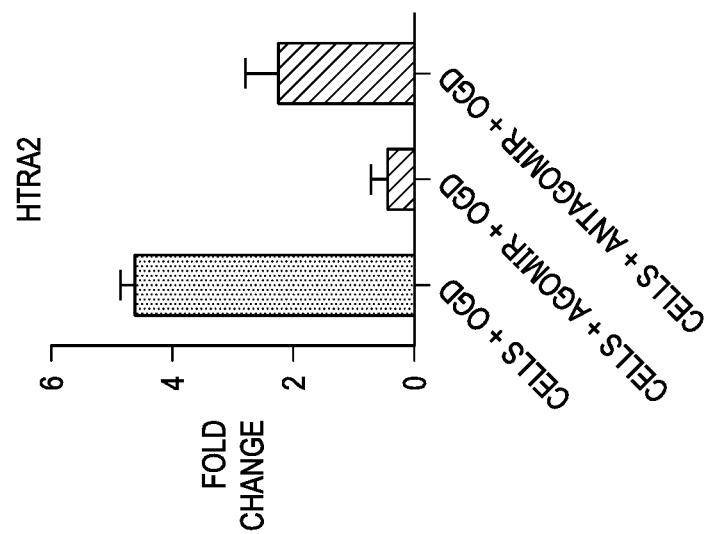

In silico analysis were performed to predict the target gene analysis for the miRNA PC-5P-12969 using TargetScan and miRanda databases. The inventors found GSK3A, PARK2, HTRA2 genes were regulated by miRNA PC-5P-12969. Further, the inventors verified expression levels of these 3 genes using qRT-PCR analysis in ischemic stroke (cells treated with oxygen glucose deprivation) cells and healthy cells. This qRT-PCR analysis revealed that abnormal mRNA levels of GSK3A, PARK2, HTRA2 genes (in ischemic cells treated with miRNA PC-5P-12969) were corrected similar to normal cells (FIGS. 8A-8C).

Cell culture and transfection. The human neuroblastoma cell line SHSY-5Y was grown in Dulbecco's modified Eagle's medium/F12 (1/1) (DMEM/F12, Gibco Life Technologies, Carlsbad, Calif., #11320), minimum essential media respectively containing 10% fetal bovine serum (FBS), penicillin (100 U/mL), streptomycin (100 µG/mL). The cultures were maintained at 37° C. in 95% air, 5% $CO_2$ in a humidified incubator. After the cells were seeded, they were allowed to grow for 24-48h or until 80% confluence in 6-well plates then they were used for experimentation. SHSY-5Y was transfected with PC-5P-12969 agomir, PC-5P-12969 antagomir, miRNA agomir negative control, miRNA antagomir negative control (all from Applied Biological Materials Inc, Canada) using Lipofectamine 2000 (Invitrogen). At 24 h transfection, cells were treated with or without 50 nM ox-LDL (Beijing Xiesheng Bio-Technology Limited, Beijing, China) for further 24 h.

Oxygen Glucose Deprivation (OGD). OGD was performed according to a previously described protocol (Vijayan et al. 2018). Culture media were replaced with deoxygenated, no glucose DMEM (Gibco, Carlsbad, Calif., #11966) and placed in hypoxia chamber (Biospherix, ProOx model 110) with 95% N2 and 5% $CO_2$ for 4 hours at 37° C. to represent OGD condition. After the appropriate time, the culture plates were removed from the hypoxia chamber. Prior to re-oxygenation, cells were washed in PBS and the medium was replaced with complete culture medium then placed in a humidified incubator at 37° C. for 20-24 hours to represent reoxygenation.

Analyses of cell viability. The number of viable cells was quantified using an AOPI staining solution in PBS Kit (Nexcelom Bioscience) according to the manufacturer's instructions.

Detection of apoptosis. Apoptosis was determined using the Annexin V-FITC/propidium iodide (PI) Apoptosis Detection Kit (Nexcelom Bioscience) according to the manufacturer's instructions. The population of Annexin V-positive cells was evaluated by Cellometer Vision.

Binding site analysis. Two computational target prediction algorithms, TargetScan 5.1(http://www.targetscan.org) and miRanda (http://www.microrna.org), were used to predict the genes targeted by miRNAs. The data-sets used were the 3' UTRs of mouse and human respectively. TargetScan was used to search for miRNA seed matches (nucleotides 2e8 from the 5' end of miRNA) in the 3' UTR sequences. miRanda was used to match the entire miRNA sequences. The miRanda parameters were set as free energy <10 kcal/mol and TargetScan parameters were set as context score percentile >50. Finally, the results predicted by the two algorithms were combined and the overlaps were calculated.

Reverse-transcription quantitative polymerase chain reaction (RT-qPCR). Total RNA was isolated from SHSY-5Y using the TriZol RT reagent (Ambion, USA) as per manufacturer instructions. cDNA synthesis and RT-qPCR were followed as described earlier (Vijayan et al., 2018). Following primers were used:

```
PC-5P-12969,                         (SEQ ID NO: 1)
5'-GCAGGAGCCGGGACTGGCTTC-3';

U6 snRNA,                            (SEQ ID NO: 2)
forward 5'-CGCTTCGGCAGCACATATACTAA-3',
                                     (SEQ ID NO: 3)
reverse 5'-TATGGAACGCTTCACGAATTTGC-3';

GSK3A,                               (SEQ ID NO: 4)
forward 5'-ATGCGTAAGCTGGACCACTG-3' and
                                     (SEQ ID NO: 5)
reverse 5'-GCTCGTCTTTCTTCTCGCCA-3';

PARK2,                               (SEQ ID NO: 6)
forward 5'-GACAGCAGGAAGGACTCACC-3' and
                                     (SEQ ID NO: 7)
reverse 5'-CACTCTTTGACAGGGGCCTT-3';

HTRA2,                               (SEQ ID NO: 8)
forward 5'-ATGATGCTGACCCTGAGTCC-3' and
                                     (SEQ ID NO: 9)
reverse 5'-TGAACATCGGGAAAGCTTGGT-3'.
```

Thus, a panel of 16 miRNAs that are either up-regulated or down-regulated in patients with an ischemic stroke or those that are at risk of suffering from the condition. A patient's blood will be screened for dysregulation among these miRNAs and a diagnosis or prophylactic measures can be taken. The 16 miRNAs are in the table below with those that are up-regulated (underlined) and down-regulated (bold). As such, the markers can be targeted by specific therapeutics that will reverse their up or down regulation during IS.

| ggo-miR-139 | hsa-miR-30d-5p | hsa-miR-22-3p | hsa-miR-23a-3p |
| hsa-miR-96-5p | hsa-miR-99a-5p | hsa-miR-122-5p | hsa-miR-186-5p |
| hsa-miR-211-5p | hsa-mir-760 | mmu-miR-5124a | mmu-mir-6240-5p |
| PC-3p-32463 | PC-3p-57664 | PC-5p-211 | PC-5p-12969 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Lozano, R., Naghavi, M., Foreman, K., Lim, S., Shibuya, K., Aboyans, V., Abraham, J., Adair, T., Aggarwal, R., Ahn, S. Y., et al. (2012) Global and regional mortality from 235 causes of death for 20 age groups in 1990 and 2010: a systematic analysis for the Global Burden of Disease Study 2010. Lancet, 380: 2095-2128.
2. Murray, C. J, Vos, T., Lozano, R., Naghavi, M., Flaxman, A. D., Michaud, C., Ezzati, M., Shibuya, K., Salomon, J. A., Abdalla, S., et al. (2012) Disability-adjusted life years (DALYs) for 291 diseases and injuries in 21 regions, 1990-2010: a systematic analysis for the Global Burden of Disease Study 2010, Lancet, 380: 2197-2223.
3. Benjamin, E. J., Blaha, M. J., Chiuve, S. E., Cushman, M., Das, S. R., Deo, R., de Ferranti, S. D., Floyd, J., Fornage, M., Gillespie, C., et al. (2017) American Heart Association Statistics Committee and Stroke Statistics Subcommittee. Heart Disease and Stroke Statistics-2017 Update: A Report From the American Heart Association. Circulation, 135:e146-e603.
4. Rosamond, W., Flegal, K., Furie, K., Go, A., Greenlund, K., Haase, N., Hailpern, S. M., Ho, M., Howard, V., Kissela, B., et al. (2008) American Heart Association Statistics Committee and Stroke Statistics Subcommittee. Heart disease and stroke statistics—2008 update: a report from the American Heart Association Statistics Committee and Stroke Statistics Subcommittee. Circulation, 117: e25-e146.
5. Pendlebury, S. T, Rothwell, P. M. (2009) Prevalence, incidence, and factors associated with pre-stroke and post-stroke dementia: a systematic review and meta-analysis. Lancet Neurol., 8:1006-1018.
6. Allan, L. M., Rowan, E. N., Firbank, M. J., Thomas, A. J., Parry, S. W., Polvikoski, T. M., O'Brien, J. T., Kalaria, R. N. (2011) Long term incidence of dementia, predictors of mortality and pathological diagnosis in older stroke survivors. Brain. 134: 3716-3727.
7. Schwarzenbach, H., Nishida, N., Calin, G. A., Pantel, K. (2014) Clinical relevance of circulating cell-free microRNAs in cancer. Nat. Rev. Clin. Oncol., 11: 145-156.
8. Jung, H. J., Suh, Y. (2014) Circulating miRNAs in aging and age related disease. J. Genet. Genom., 41: 465-472.
9. Jickling, G. C., Ander, B. P., Zhan, X., Noblett, D., Stamova, B., Liu, D. (2014) MicroRNA expression in peripheral blood cells following acute ischemic stroke and their predicted gene targets. PLoS One. 9: e99283.
10. Vijayan, M., Reddy, P. H. (2016) Peripheral biomarkers of stroke: Focus on circulatory microRNAs. Biochim. Biophys. Acta., 1862:1984-1993.
11. Nieto-Diaz, M., Esteban, F. J., Reigada, D., Muñoz-Galdeano, T., Yunta, M., Caballero-López, M., Navarro-Ruiz, R., Del Águila, A., Maza, R. M. (2014) MicroRNA dysregulation in spinal cord injury: causes, consequences and therapeutics. Front. Cell. Neurosci., 8: 53.
12. Ouyang, Y. B., Stary, C. M., Yang, G. Y., Giffard, R. (2013) MicroRNAs: innovative targets for cerebral ischemia and stroke. Curr. Drug. Targets., 14: 90.
13. Lorenzen, J. M., Thum, T. (2012) Circulating and urinary microRNAs in kidney disease. Clin. J. Am. Soc. Nephrol., 7: 1528-1533.

14. Fichtlscherer, S., Zeiher, A. M., Dimmeler, S. (2011) Circulating microRNAs: biomarkers or mediators of cardiovascular diseases? Arterioscler. Thromb. Vasc. Biol., 31: 2383-2390.
15. Laterza, O. F., Lim, L., Garrett-Engele, P. W., Vlasakova, K., Muniappa, N., Tanaka, W. K., Johnson, J. M., Sina, J. F., Fare, T. L., Sistare, F. D., Glaab, W. E. (2009) Plasma MicroRNAs as sensitive and specific biomarkers of tissue injury. Clin. Chem., 55:1977-83.
16. Cheng, Y., Zhang, C. (2010) MicroRNA-21 in cardiovascular disease. J. Cardiovasc. Transl. Res., 3: 251-255.
17. Yuan, Y., Kang, R., Yu, Y., Liu, J., Zhang, Y., Shen, C., Wang, J., Wu, P., Shen, C., Wang, Z. (2016) Crosstalk between miRNAs and their regulated genes network in stroke. Sci. Rep., 6: 20429.
18. He, W., Chen, S., Chen, X., Li, S., Chen, W. (2016) Bioinformatic Analysis of Potential microRNAs in Ischemic Stroke. J. Stroke. Cerebrovasc. Dis., 25: 1753-1759.
19. Sepramaniam, S., Tan, J. R., Tan, K. S., DeSilva, D. A., Tavintharan, S., Woon, F. P., Wang, C. W., Yong, F. L., Karolina, D. S., Kaur, P., et al. (2014) Circulating microRNAs as biomarkers of acute stroke. Int. J. Mol. Sci., 15: 1418-1432.
20. Siegel, C., Li, J., Liu, F., Benashski, S. E., McCullough, L. D. (2011) miR-23a regulation of X-linked inhibitor of apoptosis (XIAP) contributes to sex differences in the response to cerebral ischemia. Proc. Natl. Acad. Sci. USA., 108: 11662-11667.
21. Da Costa Martins, P. A., De Windt, L. J. (2012) MicroRNAs in control of cardiac hypertrophy. Cardiovasc. Res., 93: 563-572.
22. Long, G., Wang, F., Li, H., Yin, Z., Sandip, C., Lou, Y., Wang, Y., Chen, C., Wang, D. W. (2013) Circulating miR-30a, miR-126 and let-7b as biomarker for ischemic stroke in humans. BMC. Neurol., 13: 178.
23. Schmitt, A., Parlapani, E., Bauer, M., Heinsen, H., Falkai, P. (2008) Is brain banking of psychiatric cases valuable for neurobiological research? Clinics (Sao Paulo). 63: 255-266.
24. Stanzione, R., Bianchi, F., Cotugno, M., Marchitti, S., Forte, M., Busceti, C., Ryskalin, L., Fornai, F., Volpe, M., Rubattu, S. (2017) A decrease of brain microRNA-122 level is an early marker of cerebrovascular disease in the stroke-prone spontaneously hypertensive rat. Oxid. Med. Cell. Longev., 2017:1206420.
25. Liu da, Z., Jickling, G. C., Ander, B. P., Hull, H., Zhan, X., Cox, C., Shroff, N., Dykstra-Aiello, C., Stamova, B., Sharp, F. R. (2016) Elevating microRNA-122 in blood improves outcomes after temporary middle cerebral artery occlusion in rats. J. Cereb. Blood. Flow. Metab., 36: 1374-1383.
26. Wang, W., Sun, G., Zhang, L., Shi, L., Zeng, Y. (2014) Circulating microRNAs as novel potential biomarkers for early diagnosis of acute stroke in humans. J. Stroke. Cerebrovasc. Dis., 23: 2607-2613.
27. Lee, J. E., Hong, E. J., Nam, H. Y., Kim, J. W., Han, B. G., Jeon, J. P. (2011) MicroRNA signatures associated with immortalization of EBV-transformed lymphoblastoid cell lines and their clinical traits. Cell. Prolif., 44: 59-66.
28. Wheeler, H. E., Dolan, M. E. (2012) Lymphoblastoid cell lines in pharmacogenomic discovery and clinical translation. Pharmacogenomics. 13: 55-70.
29. Ziu, M., Fletcher, L., Rana, S., Jimenez, D. F., Digicaylioglu, M. (2011) Temporal differences in microRNA expression patterns in astrocytes and neurons after ischemic injury. PLoS One. 6: e14724.
30. Martinez, B., Peplow, P. V. (2016) Blood microRNAs as potential diagnostic and prognostic markers in cerebral ischemic injury. Neural. Regen. Res. 11: 1375-1378.
31. Koutsis, G., Siasos, G., Spengos, K. (2013) The emerging role of microRNA in stroke. Curr. Top. Med. Chem., 13: 1573-1588.
32. Zhao, H., Li, G., Ma, Q., Tao, Z., Wang, R., Fan, Z., Feng, Y., Ji, X., Luo, Y. (2017) MicroRNA-99a-5p in circulating immune cells as a potential biomarker for the early diagnosis of ischemic stroke. Brain. Circ., 3:21-28.
33. Griffiths-Jones, S., Saini, H. K., van Dongen, S., Enright, A. J. (2008) MiRbase: tools for microRNA genomics. Nucleic Acids Research. 36: D154-D158.
34. Griffiths-Jones, S., Grocock, R. J., van Dongen, S., Bateman, A., Enright, A. J. (2006) MiRbase: microRNA sequences, targets and gene nomenclature. Nucleic Acids Research. 34: D140-D144.
35. Griffiths-Jones, S. (2004) The microRNA Registry. Nucleic Acids Research. 32: D109-D111.
36. Kumar, S., Vijayan, M., Reddy, P. H. (2017) MicroRNA-455-3p as a potential peripheral biomarker for Alzheimer's disease. Hum. Mol. Genet., 26: 3808-3822.
37. Livak, K. J., Schmittgen, T. D. (2001) Analysis of relative gene expression data using real-time quantitative PCR and the 2 #DDCT method. Methods. 25: 402-408.
38. Vannucci, R. C., Vannucci S. J. (1997) A model of perinatal hypoxic-ischemic brain damage. Ann. N. Y. Acad. Sci., 835: 234-249.
39. Cengiz, P., Kleman, N., Uluc, K., Kendigelen, P., Hagemann, T., Akture, E., Messing, A., Ferrazzano, P., Sun, D. (2011) Inhibition of Na+/H+ exchanger isoform 1 is neuroprotective in neonatal hypoxic ischemic brain injury. Antioxid. Redox. Signal. 14: 1803-1813.
40. Uluc, K., Kendigelen, P., Fidan, E., Zhang, L., Chanana, V., Kintner, D., Akture, E., Song, C., Ye, K., Sun, D., Ferrazzano, P., et al. (2013) TrkB receptor agonist 7, 8 dihydroxyflavone triggers profound gender-dependent neuroprotection in mice after perinatal hypoxia and ischemia. CNS. Neurol. Disord. Drug. Targets. 12: 360-370.
41. Cikla, U., Chanana, V., Kintner, D. B., Udho, E., Eickhoff. J, Sun. W., Marquez. S., Covert, L., Otles, A., Shapiro, R. A., et al. (2016) ERα Signaling Is Required for TrkB-Mediated Hippocampal Neuroprotection in Female Neonatal Mice after Hypoxic Ischemic Encephalopathy (1,2,3). eNeuro. 3: 1-14.
42. Chanana, V., Tumturk, A., Kintner, D., Udho, E., Ferrazzano, P., Cengiz, P. (2016) Sex Differences in Mouse Hippocampal Astrocytes after In-Vitro Ischemia. J. Vis. Exp. 116.
43. Yu, Z., Liu, J., Guo, S., Xing, C., Fan, X., Ning, M., Yuan, J. C., Lo, E. H., Wang, X. (2009) Neuroglobin-overexpression alters hypoxic response gene expression in primary neuron culture following oxygen glucose deprivation. Neuroscience. 162: 396-403.
44. Zhu, H., Wang, Z., Xing, Y., Gao, Y., Ma, T., Lou, L., Gao, Y., Wang, S., Wang, Y. (2012) Baicalin reduces the permeability of the blood-brain barrier during hypoxia in vitro by increasing the expression of tight junction proteins in brain microvascular endothelial cells. J. Ethnopharmacol., 141: 714-720.
45. Guo, F., Wang, H., Li, L., Zhou, H., Wei, H., Jin, W., Wang, Q., Xiong, L. (2013) A novel domain of amino-Nogo-A protects HT22 cells exposed to oxygen glucose deprivation by inhibiting NADPH oxidase activity. Cell. Mol. Neurobiol., 33:443-452.
46. Alluri, H., Anasooya Shaji, C., Davis, M. L., Tharakan, B. (2015) Oxygen-glucose deprivation and reoxygenation as an in vitro ischemia-reperfusion injury model for studying blood-brain barrier dysfunction. J. Vis. Exp., 99:e52699.

47. Lewis, B. P., Burge, C. B., Bartel, D. P. (2005) Conserved seed pairing, often flanked by adenosines, indicates that thousands of human genes are microRNA targets. Cell. 120: 15-20.

48. Huang, D. W., Sherman, B. T., Lempicki, R. A. (2009) Systematic and integrative analysis of large gene lists using DAVID Bioinformatics Resources. Nature. Protoc., 4: 44-57.

49. Tan, L., Yu, J. T., Liu, Q. Y., Tan, M. S., Zhang, W., Hu, N., Wang, Y. L., Sun, L., Jiang, T., Tan, L. (2014) Circulating miR-125b as a biomarker of Alzheimer's disease. J. Neurol. Sci., 336: 52-56.

What is claimed is:

1. A method to reduce or inhibit ischemic stroke in a human, the method comprising:
   (a) obtaining a blood sample from the human and determining the presence of microRNAs in the blood sample associated with ischemic stroke;
   (b) based on the microRNAs determined to be associated with ischemic stroke in step (a), selecting microRNAs to upregulate selected from the group consisting of hsa-miR-22-3p, PC-5p-12969 and combinations thereof; and
   (c) based on the microRNAs determined to be associated with ischemic stroke in need of upregulation, administering an oligonucleotide that: upregulates hsa-miR-22-3p, PC-5p-12969, or both hsa-miR-22-3p and PC-5p-12969 to the mammal in an amount sufficient to reduce or inhibit ischemic stroke in the human.

2. The method of claim 1, wherein the oligonucleotide that modified the expression of the one or more microRNA is a mimic.

3. The method of claim 2, wherein the oligonucleotide contains a non-naturally occurring modification comprising modifications or substitutions of: (1) the ribose or other sugar units, (2) bases, or (3) the backbone, selected from: one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions, partially or completely modified backbones, fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, sugar modifications 2' O methyl (2'-O-methylnucleotides), 2'-O-methyloxyethoxy (2'-O-MOE), a 2'-O-alkyl modified sugar moiety, or a bicyclic sugar moiety, nucleotide mimetics, peptide nucleic acids (PNA), morpholino nucleic acids, cyclohexenyl nucleic acids, anhydrohexitol nucleic acids, glycol nucleic acid, threose nucleic acid, and locked nucleic acids (LNA), and a combinations of two or more of any of the foregoing.

4. The method of claim 2, wherein the oligonucleotide comprises a sequence having at least 88, 92, 93, 94, 95, 96, 97, 98, or 99% identity to hsa-miR-22-3p, PC-5p-12969, or both hsa-miR-22-3p and PC-5p-12969.

5. The method of claim 2, wherein the oligonucleotide targets one or more regulatory regions that downregulate messenger RNA transcription.

6. The method of claim 1, further comprising measuring the levels the miRNAs for PC-3p-57664, PC-5p-12969, hsa-miR-122-5p and hsa-miR-211-5p to determine if they were upregulated or downregulated as a result of the treatment.

7. The method of claim 1, wherein the oligonucleotide further comprises a pharmaceutically acceptable excipient, salts, or carrier, and is optionally formulated for intravenous, intramuscular, intraperitoneal, oral, subcutaneous, enteral or parenteral administration.

8. A method to reduce or inhibit ischemic damage in a human suspected of having ischemic damage of a tissue, the method comprising:
(a) obtaining a blood sample from the human and determining the microRNAs in the blood sample associated with ischemic stroke;
(b) based on the microRNAs determined to be associated with ischemic stroke in step (a), selecting microRNAs to upregulate selected from the group consisting of hsa-miR-22-3p, PC-5p-12969 and combinations thereof; and
(c) based on the microRNAs determined to be associated with ischemic stroke in need of upregulation, administering one or more agents that modify the expression of hsa-miR-22-3p, PC-5p-12969, or both hsa-miR-22-3p and PC-5p-12969, to the human with ischemic damage, wherein the agent is an oligonucleotide.

9. The method of claim 8, wherein the oligonucleotide that modified the expression of the one or more microRNA microRNA is a mimic.

10. The method of claim 9, wherein the oligonucleotide contains a non-naturally occurring modification comprising modifications or substitutions of: (1) the ribose or other sugar units, (2) bases, or (3) the backbone, selected from: one or more phosphorothioate, phosphorodithioate, phosphodiester, methyl phosphonate, phosphoramidate, methylphosphonate, phosphotriester, phosphoroaridate, morpholino, amidate carbamate, carboxymethyl, acetamidate, polyamide, sulfonate, sulfonamide, sulfamate, formacetal, thioformacetal, and/or alkylsilyl substitutions, partially or completely modified backbones, fully modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, sugar modifications 2'-O-methyl (2'-O-methylnucleotides), 2'-O-methyloxyethoxy (2'-O-MOE), a 2'-O-alkyl modified sugar moiety, or a bicyclic sugar moiety, nucleotide mimetics, peptide nucleic acids (PNA), morpholino nucleic acids, cyclohexenyl nucleic acids, anhydrohexitol nucleic acids, glycol nucleic acid, threose nucleic acid, and locked nucleic acids (LNA), and a combinations of two or more of any of the foregoing.

11. The method of claim 9, wherein the oligonucleotide comprises a sequence having at least 88, 92, 93, 94, 95, 96, 97, 98, or 99% identity to hsa-miR-22-3p, PC-5p-12969, or both hsa-miR-22-3p and PC-5p-12969.

12. The method of claim 9, wherein the oligonucleotide targets one or more regulatory regions that downregulate messenger RNA transcription.

13. The method of claim 8, further comprising the steps of treating the patient for ischemic stroke and measuring the levels the miRNAs for PC-3p-57664, PC-5p-12969, hsa-miR-122-5p and hsa-miR-211-5p to determine if they were upregulated or downregulated as a result of the treatment.

14. The method of claim 8, wherein the oligonucleotide further comprises a pharmaceutically acceptable excipient, salts, or carrier, and is optionally formulated for intravenous, intramuscular, intraperitoneal, oral, subcutaneous, enteral or parenteral administration.

\* \* \* \* \*

SEQUENCE LISTING

```
<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
gcaggagccg ggactggctt c                                              21

<210> SEQ ID NO 2
<211> LENGTH: 23
<212> TYPE: DNA
<213> ORGANISM: Artificial Sequence
<220> FEATURE:
<223> OTHER INFORMATION: Synthetic primer

<400> SEQUENCE: 2
cgcttcggca gcacatatac taa                                            23

<210> SEQ ID NO 3
<211> LENGTH: 23
<212> TYPE: DNA
<213> ORGANISM: Artificial Sequence
<220> FEATURE:
<223> OTHER INFORMATION: Synthetic primer

<400> SEQUENCE: 3
tatggaacgc ttcacgaatt tgc                                            23

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
atgcgtaagc tggaccactg                                                20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
gctcgtcttt cttctcgcca                                                20

<210> SEQ ID NO 6
<211> LENGTH: 20
<212> TYPE: DNA
<213> ORGANISM: Artificial Sequence
<220> FEATURE:
```

```
<223> OTHER INFORMATION: Synthetic primer

<400> SEQUENCE: 6
gacagcagga aggactcacc                                        20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
cactctttga cagggccttt                                        20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
atgatgctga ccctgagtcc                                        20

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
tgaacatcgg gaaagcttgg t                                      21
```